United States Patent [19]
Lilley et al.

[11] Patent Number: 5,891,085
[45] Date of Patent: Apr. 6, 1999

[54] NOZZLE ASSEMBLY WITH LOST MOTION CONNECTION FOR MEDICAL INJECTOR ASSEMBLY

[75] Inventors: Stephen John Lilley; Hugh Francis Taylor, both of Sawston; David Reginald Theobald, Huntingdon, all of United Kingdom; Craig J. Carlson, Andover; David I. Rosen, Arlington, both of Mass.; Thomas R. Johnson, Milford, N.H.

[73] Assignee: Medi-Ject Corporation, Minneapolis, Minn.

[21] Appl. No.: 780,917

[22] Filed: Jan. 9, 1997

Related U.S. Application Data

[62] Division of Ser. No. 369,812, Jan. 9, 1995, Pat. No. 5,599,302.

[51] Int. Cl.[6] .................................................. A61M 5/30
[52] U.S. Cl. .......................... 604/68; 604/73; 604/140; 604/147
[58] Field of Search .......................... 604/68–73, 133–5, 604/140, 141, 143, 146, 147, 206, 207

[56] References Cited

U.S. PATENT DOCUMENTS

| | | |
|---|---|---|
| D. 304,616 | 11/1989 | Dunlap et al. . |
| D. 349,958 | 8/1994 | Hollis et al. . |
| 396,107 | 1/1889 | Nickerson . |
| 489,757 | 1/1893 | Reilly . |
| 1,567,517 | 12/1925 | Kisbey . |
| 1,973,706 | 9/1934 | Hawley . |
| 2,322,244 | 6/1943 | Lockhart . |
| 2,322,245 | 6/1943 | Lockhart . |
| 2,380,534 | 7/1945 | Lockhart . |
| 2,390,246 | 12/1945 | Folkman . |
| 2,398,544 | 4/1946 | Lockhart . |
| 2,413,303 | 12/1946 | Folkman . |
| 2,459,875 | 1/1949 | Folkman . |
| 2,547,099 | 4/1951 | Smoot . |
| 2,605,763 | 8/1952 | Smoot . |
| 2,635,602 | 4/1953 | Hein . |
| 2,653,602 | 9/1953 | Smoot . |
| 2,670,121 | 2/1954 | Scherer et al. . |
| 2,671,347 | 3/1954 | Scherer . |

(List continued on next page.)

FOREIGN PATENT DOCUMENTS

| | | |
|---|---|---|
| 2028870 | 5/1991 | Canada . |
| 2071115 | 12/1992 | Canada . |
| 0 157 906 | 10/1985 | European Pat. Off. . |
| 0 460 961 | 6/1991 | European Pat. Off. . |
| 2254153A | 5/1974 | Germany . |
| 76202162 | 5/1986 | Taiwan . |
| 959397 | 6/1964 | United Kingdom . |
| 2249159 | 1/1994 | United Kingdom . |
| WO 93/03779 | 3/1993 | WIPO . |
| WO 95/03844 | 2/1995 | WIPO . |

OTHER PUBLICATIONS

Catalog: Hoechst Celanese—Advanced Materials Group, "Vectra® Liquid Crystal Polymer".
Catalog: Industrial Gas Springs, Ltd.

*Primary Examiner*—Wynn Wood Coggins
*Assistant Examiner*—Jennifer R. Sadula
*Attorney, Agent, or Firm*—Pennie & Edmonds LLP

[57] ABSTRACT

A needleless injection system and method for injecting a medical product including a needleless injection device having a nozzle assembly defining an ampule chamber for holding medication, an energy device for pushing medication out of the nozzle assembly, and an energy device actuating mechanism is disclosed. These components are operatively contained in a housing configured for hand held operation. The energy device is a self-contained gas spring operatively connected to a plunger operating within the ampule chamber. The gas spring is preferably stepped which can be used in many different applications, an air gun being one. The injection device can be provided with a coupling device for coupling a medication supply vial to the nozzle assembly. The nozzle assembly is removably situated in the housing with the plunger removable therewith.

14 Claims, 11 Drawing Sheets

U.S. PATENT DOCUMENTS

| | | |
|---|---|---|
| 2,681,653 | 6/1954 | Kuhne . |
| 2,688,968 | 9/1954 | Scherer . |
| 2,699,166 | 1/1955 | Dickinson, Jr. et al. . |
| 2,704,542 | 3/1955 | Scherer . |
| 2,704,543 | 3/1955 | Scherer . |
| 2,705,953 | 4/1955 | Potez . |
| 2,714,887 | 8/1955 | Venditty . |
| 2,717,597 | 9/1955 | Hein, Jr. . |
| 2,737,946 | 3/1956 | Hein, Jr. . |
| 2,754,818 | 7/1956 | Scherer . |
| 2,762,369 | 9/1956 | Venditty . |
| 2,762,370 | 9/1956 | Venditty . |
| 2,764,977 | 10/1956 | Ferguson . |
| 2,789,839 | 4/1957 | Siebert . |
| 2,798,485 | 7/1957 | Hein, Jr. . |
| 2,798,486 | 7/1957 | Hein, Jr. . |
| 2,800,903 | 7/1957 | Smoot . |
| 2,816,543 | 12/1957 | Venditty et al. . |
| 2,816,544 | 12/1957 | Scherer et al. . |
| 2,820,655 | 1/1958 | Hileman . |
| 2,821,193 | 1/1958 | Ziherl et al. . |
| 2,821,981 | 2/1958 | Ziherl et al. . |
| 2,825,332 | 3/1958 | Johnson . |
| 2,902,994 | 9/1959 | Scherer . |
| 2,921,582 | 1/1960 | Sadd . |
| 2,928,390 | 3/1960 | Venditty et al. . |
| 3,057,349 | 10/1962 | Ismach . |
| 3,066,670 | 12/1962 | Stauffer . |
| 3,115,133 | 12/1963 | Morando . |
| 3,123,070 | 3/1964 | Kath . |
| 3,129,708 | 4/1964 | Krantz . |
| 3,130,723 | 4/1964 | Venditty et al. . |
| 3,131,692 | 5/1964 | Love . |
| 3,138,157 | 6/1964 | Ziherl et al. . |
| 3,140,713 | 7/1964 | Ismach . |
| 3,147,967 | 9/1964 | Bougeard . |
| 3,167,071 | 1/1965 | Venditty . |
| 3,189,029 | 6/1965 | Stephens . |
| 3,202,151 | 8/1965 | Kath . |
| 3,245,703 | 4/1966 | Manly . |
| 3,292,622 | 12/1966 | Banker . |
| 3,308,818 | 3/1967 | Rufkowski . |
| 3,330,276 | 7/1967 | Gordon . |
| 3,330,277 | 7/1967 | Gabriels . |
| 3,335,722 | 8/1967 | Lowry et al. . |
| 3,343,538 | 9/1967 | Morley . |
| 3,353,537 | 11/1967 | Knox et al. . |
| 3,399,759 | 9/1968 | Love . |
| 3,406,684 | 10/1968 | Tsujino . |
| 3,419,007 | 12/1968 | Love . |
| 3,424,154 | 1/1969 | Kinsley . |
| 3,461,867 | 8/1969 | Zimmet et al. . |
| 3,476,110 | 11/1969 | Yahmer . |
| 3,490,451 | 1/1970 | Yahner . |
| 3,507,276 | 4/1970 | Burgess . |
| 3,518,990 | 7/1970 | Banker . |
| 3,521,633 | 7/1970 | Yahner . |
| 3,526,225 | 9/1970 | Hayamamachi . |
| 3,527,212 | 9/1970 | Clarke . |
| 3,557,784 | 1/1971 | Shields . |
| 3,561,443 | 2/1971 | Banker . |
| 3,625,208 | 12/1971 | Frost et al. . |
| 3,659,587 | 5/1972 | Baldwin . |
| 3,688,765 | 9/1972 | Gasaway . |
| 3,714,943 | 2/1973 | Yanof et al. . |
| 3,768,472 | 10/1973 | Hodosh et al. . |
| 3,779,371 | 12/1973 | Rovinski . |
| 3,782,380 | 1/1974 | Van Der Gaast . |
| 3,783,895 | 1/1974 | Weichselbaum . |
| 3,805,783 | 4/1974 | Ismach . |
| 3,827,601 | 8/1974 | Magrath et al. . |
| 3,838,689 | 10/1974 | Cohen . |
| 3,908,651 | 9/1975 | Fudge . |
| 3,938,520 | 2/1976 | Scislowicz et al. . |
| 3,945,379 | 3/1976 | Pritz et al. . |
| 3,945,383 | 3/1976 | Bennet et al. . |
| 4,059,107 | 11/1977 | Iriguchi et al. . |
| 4,089,334 | 5/1978 | Schwebel et al. . |
| 4,141,675 | 2/1979 | O'Neill . |
| 4,328,802 | 5/1982 | Curley et al. . |
| 4,387,879 | 6/1983 | Tauschinski . |
| 4,421,508 | 12/1983 | Cohen . |
| 4,447,225 | 5/1984 | Taff et al. . |
| 4,500,075 | 2/1985 | Tsuchiya et al. . |
| 4,505,709 | 3/1985 | Froning et al. . |
| 4,507,113 | 3/1985 | Dunlap . |
| 4,518,385 | 5/1985 | Lindmayer et al. ....................... 604/68 |
| 4,561,856 | 12/1985 | Cochran ................... 604/143 |
| 4,588,403 | 5/1986 | Weiss et al. . |
| 4,596,556 | 6/1986 | Morrow et al. . |
| 4,619,651 | 10/1986 | Kopfer et al. . |
| 4,623,332 | 11/1986 | Lindmayer et al. ....................... 604/68 |
| 4,626,242 | 12/1986 | Fejes et al. . |
| 4,662,878 | 5/1987 | Lindmayer . |
| 4,675,020 | 6/1987 | McPhee . |
| 4,680,027 | 7/1987 | Parson et al. ............................. 604/68 |
| 4,709,686 | 12/1987 | Taylor et al. . |
| 4,722,728 | 2/1988 | Dixon . |
| 4,744,786 | 5/1988 | Hooven . |
| 4,768,568 | 9/1988 | Fournier et al. . |
| 4,771,758 | 9/1988 | Taylor et al. . |
| 4,775,173 | 10/1988 | Sauer . |
| 4,790,824 | 12/1988 | Morrow et al. . |
| 4,834,149 | 5/1989 | Fournier et al. . |
| 4,850,967 | 7/1989 | Cosmai . |
| 4,863,427 | 9/1989 | Cocchi ................... 604/110 |
| 4,874,367 | 10/1989 | Edwards . |
| 4,883,483 | 11/1989 | Lindmayer . |
| 4,909,488 | 3/1990 | Seibert et al. . |
| 4,923,072 | 5/1990 | Rilliet . |
| 4,940,460 | 7/1990 | Casey et al. . |
| 4,941,880 | 7/1990 | Burns ................... 604/143 |
| 4,948,104 | 8/1990 | Wirges . |
| 4,950,240 | 8/1990 | Greenwood et al. . |
| 4,989,905 | 2/1991 | Rajecki . |
| 5,024,656 | 6/1991 | Gasaway et al. .......................... 604/70 |
| 5,031,266 | 7/1991 | Tillman et al. . |
| 5,041,715 | 8/1991 | Muller . |
| 5,061,263 | 10/1991 | Yamazaki et al. . |
| 5,062,830 | 11/1991 | Dunlap . |
| 5,064,413 | 11/1991 | McKinnon et al. . |
| 5,073,165 | 12/1991 | Edwards . |
| 5,085,332 | 2/1992 | Gettig et al. . |
| 5,116,313 | 5/1992 | McGregor . |
| 5,161,786 | 11/1992 | Cohen . |
| 5,165,560 | 11/1992 | Ennis, III et al. . |
| 5,176,406 | 1/1993 | Straghan . |
| 5,181,912 | 1/1993 | Hammett . |
| 5,188,599 | 2/1993 | Botich et al. ............................. 604/10 |
| 5,193,517 | 3/1993 | Taylor et al. . |
| 5,209,362 | 5/1993 | Lutzker . |
| 5,226,882 | 7/1993 | Bates ................... 604/110 |
| 5,279,576 | 1/1994 | Loo et al. ................... 604/187 |
| 5,281,202 | 1/1994 | Weber et al. ................... 604/132 |
| 5,292,308 | 3/1994 | Ryan . |
| 5,304,128 | 4/1994 | Haber et al. . |
| 5,312,335 | 5/1994 | McKinnon et al. . |
| 5,312,577 | 5/1994 | Peterson et al. . |
| 5,334,144 | 8/1994 | Alchas et al. ................... 604/68 |
| 5,352,203 | 10/1994 | Vallelunga et al. . |
| 5,356,380 | 10/1994 | Hoekwater et al. . |
| 5,383,851 | 1/1995 | McKinnon, Jr. et al. . |

| | | | |
|---|---|---|---|
| 5,399,163 | 3/1995 | Peterson et al. . | |
| 5,413,471 | 5/1995 | Yamauchi . | |
| 5,454,409 | 10/1995 | McAffer et al. . | |
| 5,480,381 | 1/1996 | Weston | 604/68 |
| 5,499,972 | 3/1996 | Parsons | 604/68 |
| 5,503,627 | 4/1996 | McKinnon et al. | 604/72 |
| 5,520,639 | 5/1996 | Peterson et al. | 604/68 |
| 5,569,189 | 10/1996 | Parsons . | |

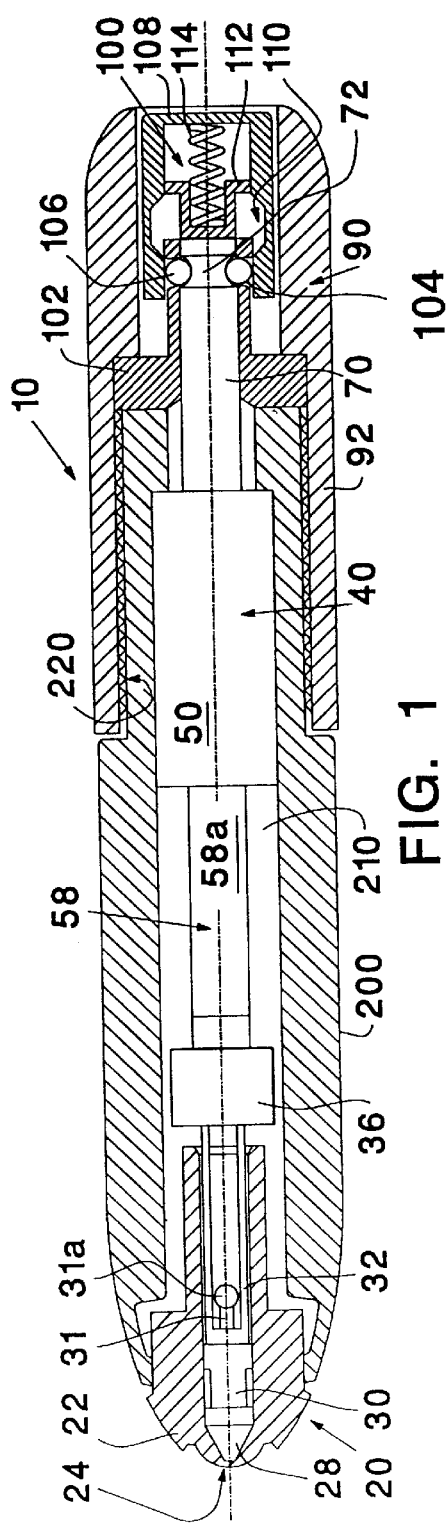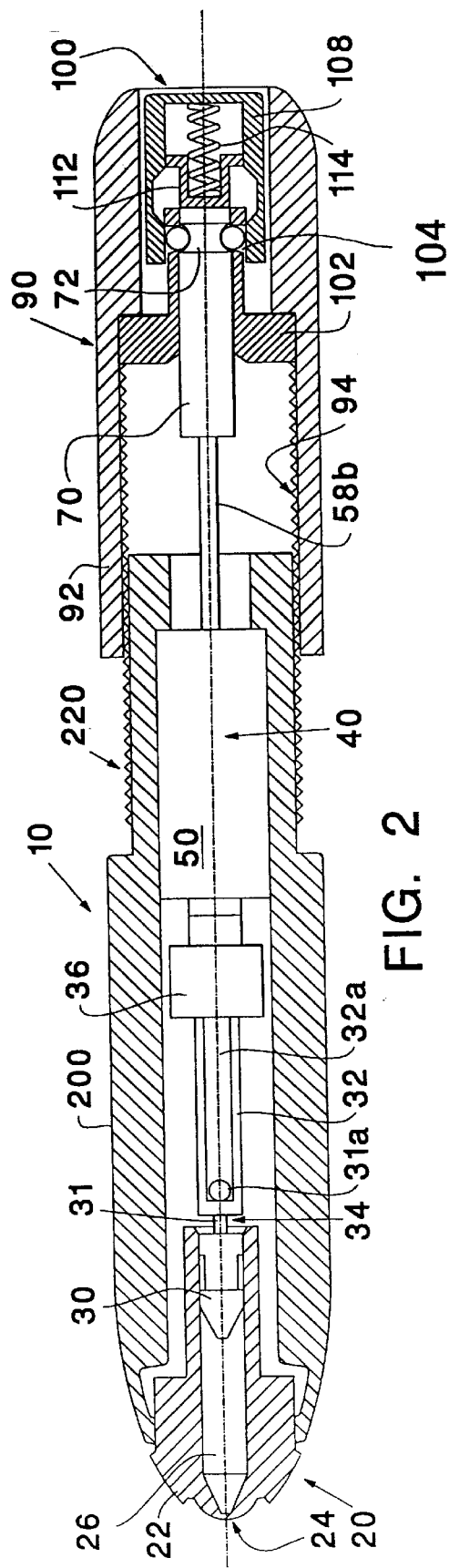

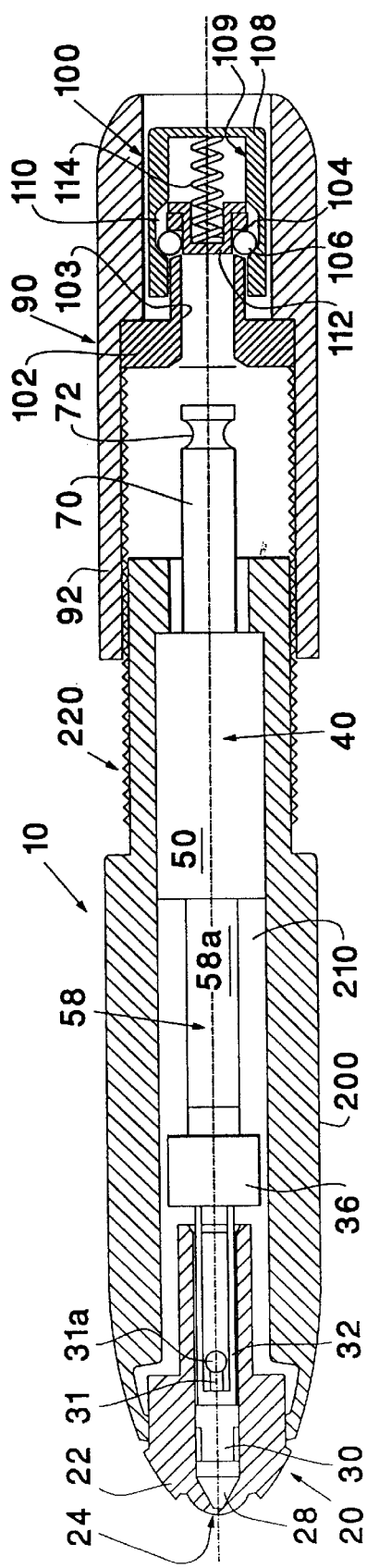
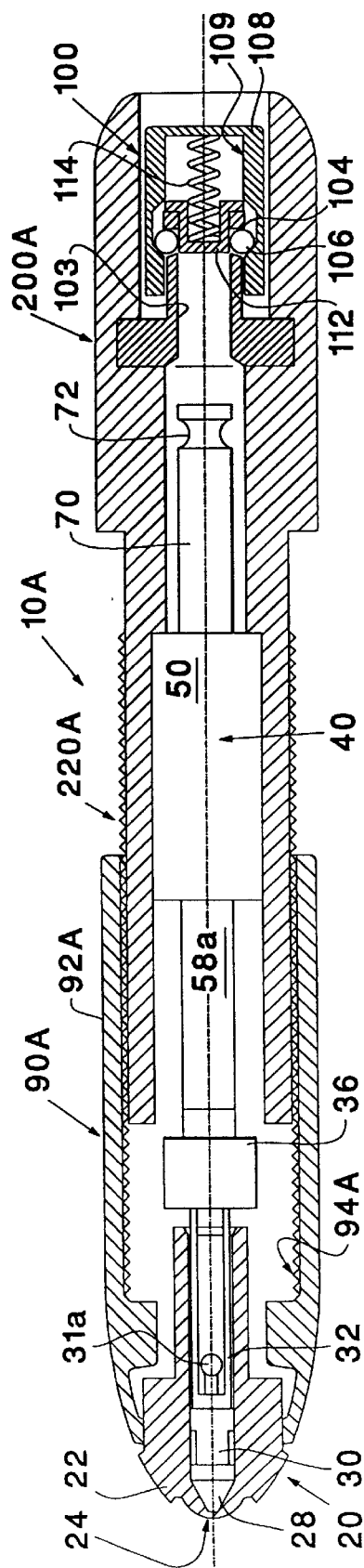

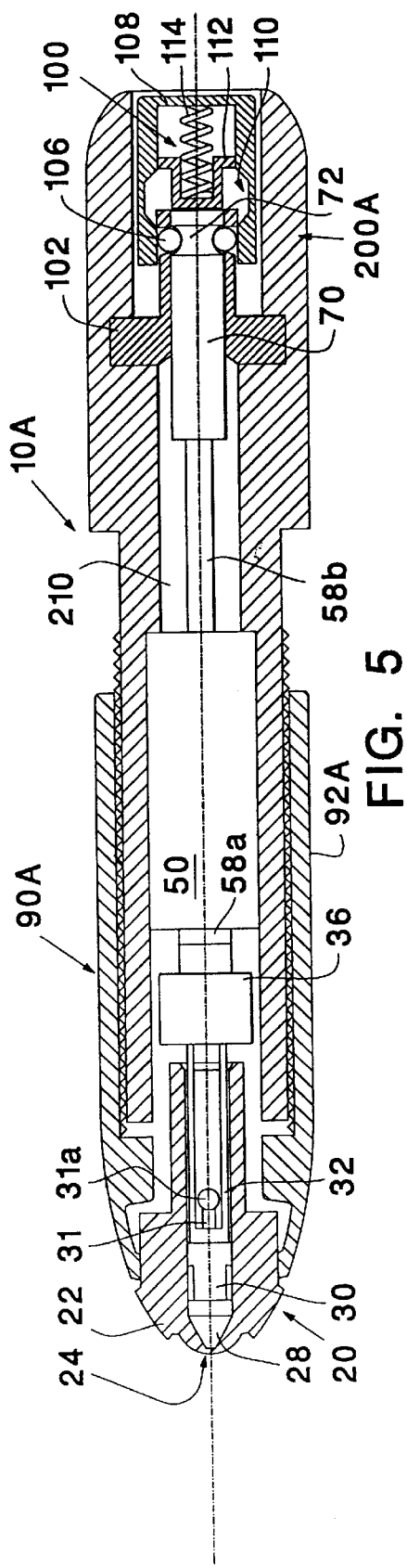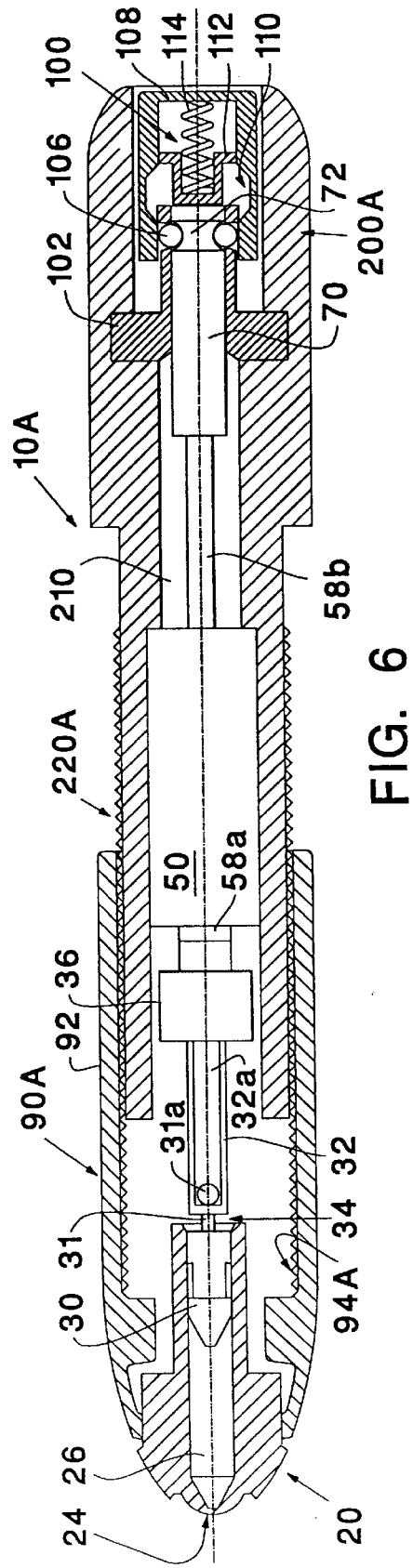

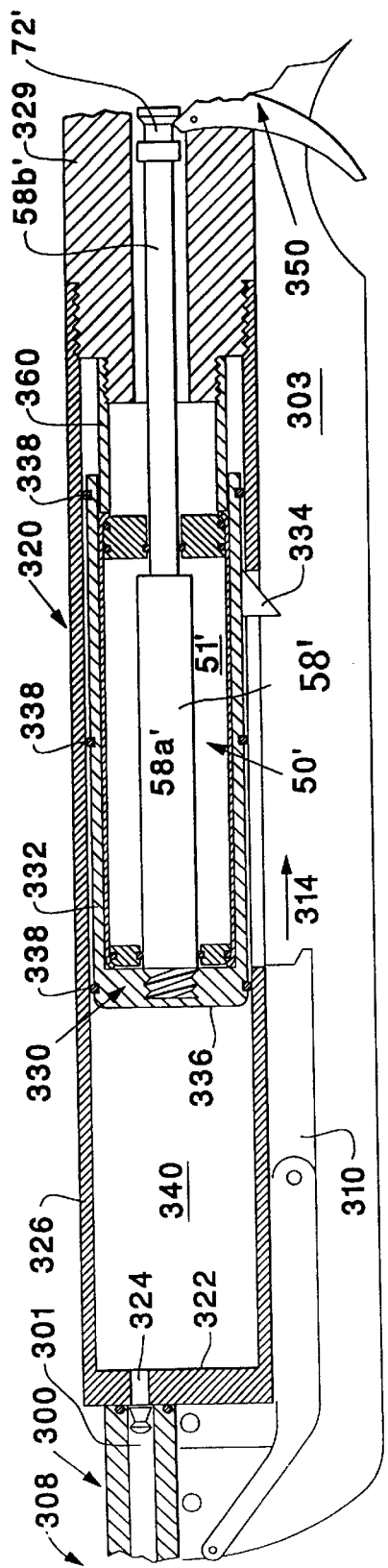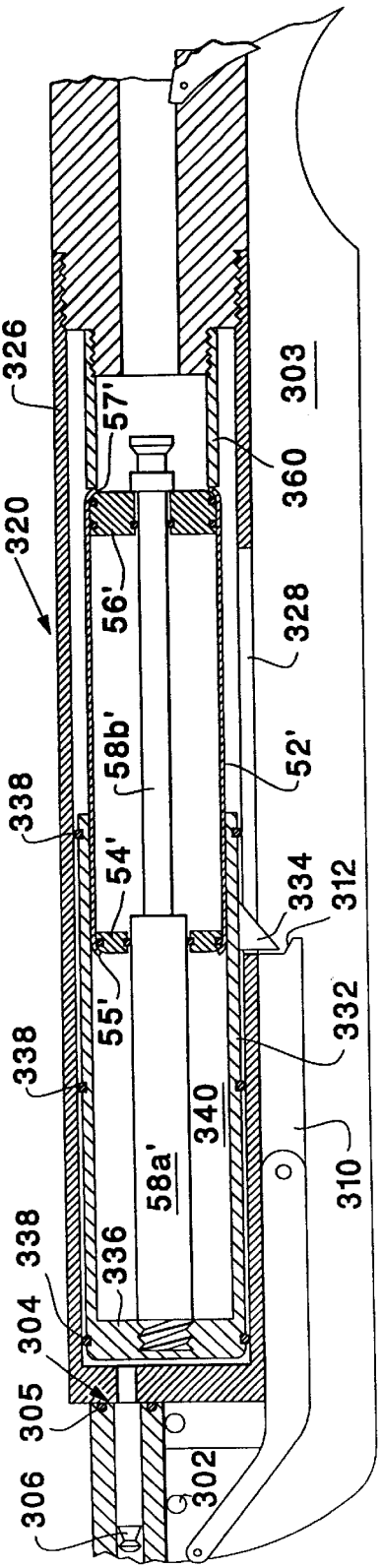

NOZZLE ASSEMBLY WITH LOST MOTION CONNECTION FOR MEDICAL INJECTOR ASSEMBLY

This is a divisional of application Ser. No. 08/369,812, filed Jan. 9, 1995 which issued as U.S. Pat. No. 5,599,302 on Feb. 4, 1997.

TECHNICAL FIELD

The present invention relates to a needleless injection system for injecting medication or the like, and in particular to a needleless injection device or injector employing a gas spring to force the medication out of the injector. The present gas spring can be used in the needleless injector as well as other devices such as an air gun. The injection system also includes a disposable, quick release coupling device for coupling a medication supply vial to the needleless injector or the like.

BACKGROUND

Different types of needleless injection devices are described, for instance, in U.S. Pat. No. 5,062,830 issued to Dunlap; U.S. Pat. No. 4,790,824 to Morrow et al.; U.S. Pat. No. 4,623,332 to Lindmayer et al.; U.S. Pat. No. 4,421,508 to Cohen; U.S. Pat. No. 4,089,334 to Schwebel et al.; U.S. Pat. No. 3,688,765 to Gasaway; U.S. Pat. No. 3,115,133 to Morando; U.S. Pat. No. 2,816,543 to Venditty et al.; and U.S. Pat. No. 2,754,818 to Scherer. These injectors have been contemplated to administer medication as a fine, high velocity jet, delivered under sufficient pressure to enable the jet to pass through the skin tissue without requiring a hypodermic needle. These injectors typically have a nozzle assembly having an internal chamber for holding medication. The nozzle member has an orifice through which a jet stream of medication is forced out from the chamber typically using a plunger attached to an energy source, most commonly a coil spring, as described for instance in the aforementioned '830, '543 and '818 patents.

Needleless injectors provide a relatively painless and efficient way of administering medication to a percutaneous or subcutaneous tissue zone, for example, and therefore are deemed better suited for such use. For example, persons afflicted with diabetes mellitus need to take one or more daily doses of insulin to maintain an appropriate glycemic balance. When a hypodermic needle is used, due to the natural aversion to piercing oneself with the needle, patient compliance with physician's dosage regimen can be hampered. On the other hand, when a needleless injector is used, since there is no needle, any apprehension of piercing oneself with a needle is substantially eliminated, allowing the patient to better comply with the dosage regimen. Moreover, repeated needle injection to the same tissue area may lead to skin or tissue damage. The needleless injector also affords a further advantage in that the medication is dispersed through a greater volume of subcutaneous tissue than when a bolus injection is introduced through a conventional hypodermic needle.

Further, with the advent of the spread of AIDS, hepatitis and other viral diseases, medical communities have become quite concerned over the possibility of accidental "sticks" involved with use of conventional hypodermic needles and problems associated with disposing the same. Special waste containers or the like thus have been mandated to collect and dispose used needles. The needless injection devices eliminate the problems associated with used needles and thus are better suited for use.

Notwithstanding the advantages obtained with needleless injectors in general, the presently known portable needleless injectors, however, do pose certain shortcomings. These include the inability to provide sufficient and generally substantially constant pressure over the period during which the medication is ejected from the nozzle assembly. Consequently, the medication within the nozzle assembly may not be fully injected to a target zone if the spring force is not sufficiently high throughout the injection period, which can lead to a "wet" injection. In this regard, the aforementioned '332 patent uses a large number of axially aligned disk springs in attempting to defeat this shortcoming. However, these disk springs not only make the injector somewhat heavy, they are much more complicated and they do not necessarily output a uniform compression load. In attempting to overcome the problems associated with the disk springs as a power source, a simpler and stronger coil spring has been contemplated in place of the disk springs, as disclosed for example in U.S. Pat. No. 4,722,728 issued to Dixon. The coil spring, however, has aforementioned shortcomings in that they do not produce a substantially constant ejection pressure output.

In addition, a coil spring operated system is limited in terms of the amount of maximum force that can be exerted on the plunger for a given size thereof. Generally, it is desirable to have a more compact, user friendly device, but if a larger force is desired, the size of the coil spring has to be accordingly increased, contrary to the desirability of compactness. Moreover, for a given compact size, greater force variation is desired to allow for injection of a variety of medications and doses. The known devices do not remedy the deficiencies evident in these trade offs.

In the aforementioned '508 patent, in attempting to regulate the amount of pressure applied to the plunger of a needleless injector, a powered vacuum-compression unit is used as an energy source. While the pressure can be regulated using such a device, the portability and size are severely compromised as a separate power supply is needed to run the vacuum-compression unit.

Another energy source previously contemplated in this field is a gas propellant, such as a $CO_2$ cartridge, as described in the aforementioned '824 and '765 patents, where the $CO_2$ gas from the cartridge is used to propel the plunger and expel medication out of the nozzle assembly. However, the drawback with the $CO_2$ cartridge is that it can only generate a limited pressure range and the pressure output is highly sensitive to the ambient temperature. The pressure of $CO_2$ fluctuates with the change in the ambient temperature. In this regard, to properly operate the device, independent of the ambient temperature, it becomes necessary to include a pressure regulator device, further complicating the device.

In the aforementioned '334 patent, in attempting to generate pressure necessary to force the plunger, a gas generating pyrotechnic charge is contemplated. Specifically, the charge is detonated to produce pressurized gas acting upon the plunger. Again, this type of device has many shortcomings. First, the pressure generated from the detonating charge can be unreliable in that the charge does not necessarily produce uniform pressure each time it is detonated. For instance, different batches of detonating charges can produce different pressure levels even if a same amount of charge is used inasmuch as different charges burn at different rates. Another drawback is that since the gas acts directly on the plunger, there is a possibility of the discharged gas seeping through the seals of the plunger and into the medication and contaminating it. Even worse, there is the undesired possibility of the discharged gas being injected through the skin, especially if the pressure exceeds the operational limits.

Even pneumatic types of energy source have been contemplated, as described for example in U.S. Pat. No. 2,764,977 issued to Ferguson; U.S. Pat. No. 2,737,946 issued to Henin, Jr.; U.S. Pat. No. 2,322,245 and U.S. Pat. No. 2,380,534 issued to Lockhart for propelling a plunger of a needleless injector. Specifically, a pressurized chamber defined by the injector's main housing is further compressed manually to store energy, which is to propel the plunger. However, they have not been designed to deliver medication under substantially constant pressure throughout the injection period, suffering the same predicament of the coil operated devices.

It is desirable to simplify the needleless injector and the use thereof as much as possible, as well as making the same compact and light for portability. Such improvements make the device user friendly to encourage rather than discourage use of the device. In this regard, U.S. Pat. No. 4,507,113 issued to Dunlap; and U.S. Pat. No. 4,883,483 and U.S. Pat. No. 4,662,878 issued to Lindmayer describe an adapter for filling the internal chamber of a nozzle assembly from a medication supply vial directly through the ejection orifice. This not only results in essentially zero residual medication retention in the injector following the dispensing of the medication, but also eliminates any need for a complex valve arrangement or medication supply arrangement described for example in U.S. Pat. No. 4,059,107 issued to Iriguchi et al. and U.S. Pat. No. 3,908,651 issued to Fudge that otherwise needs to be built into the needleless injector.

The adapter described in the aforementioned '113 patent uses a bayonet mount that requires alignment and rotation. Similarly, the adapters described in the aforementioned '483 and '878 patents have a threaded mount that also has a rotary connection. Another drawback with these adapters is that a sharp hollow probe protrudes beyond the length of the main body, which if not handled carefully can injure the user, i.e., needle sticking.

It would be desirable to proliferate use of needleless injectors by providing a safe, simple disposable adapter or coupling device that can be quickly connected and disconnected to the injector. We have invented such a coupling device.

We have invented a needleless injection device that can overcome the above noted drawbacks by providing additional improvements to presently available needleless injectors. Moreover, we have invented an improved gas spring that can be used with any needleless injection device and other devices. These devices can include a projectile launching device such as an air gun. In this regard, U.S. Pat. Nos. 5,193,517; 4,771,758; and 4,709,686 all issued to Taylor et al. disclose some examples of known gas springs for use in air guns.

SUMMARY OF THE INVENTION

The present invention is drawn to a needleless injection system which includes a needleless device for injecting a medical product, in particular, to a portable hand held device for injecting a medical product into a patient. The present system can also include a coupling device for coupling a medication supply vial to a nozzle assembly of a needleless injection device or the like. The present invention is additionally drawn to an improved gas spring that can be used with devices requiring an energy source, including a needleless injector and a projectile launching device such as an air gun.

The needleless injector according to the present invention comprises a nozzle assembly having an ampule chamber for holding the medical product and an energy mechanism or energy means. The nozzle assembly has an orifice in fluid communication with the ampule chamber for allowing passage of the medical product in and out of the ampule chamber. The nozzle assembly is preferably removably connected and can be prefilled with a medical product if desired or can even be of a disposable type.

A pressure wall member, preferably a plunger, is movably disposed within the ampule chamber holding the medical product. The energy mechanism comprises a gas spring dimensioned and configured to selectively couple to the pressure wall member, which preferably is discrete and self-contained for replaceability. The gas spring rapidly moves the pressure wall member and forces the medical product out of the ampule chamber at a substantially uniform pressure.

According to the present invention, the gas spring comprises a gas spring pressure chamber defined by a tubular sleeve and a pair of sealed ends, preferably end plugs, sealingly enclosing the tubular sleeve, and a piston extending through the end plugs and occupying a portion of the gas spring chamber. The gas spring chamber is pressurized with gas, preferably nitrogen. The piston is slidable relative to the ends or end plugs, but seals the chamber to retain the pressure in the gas spring chamber. The piston has a first piston portion and a second piston portion, the first piston portion being larger than the second piston portion. At least a part of the second piston portion occupies the gas spring chamber when the piston is at its neutral condition, where the gas spring chamber is further compressed by moving the larger first piston portion into the gas spring chamber. Preferably, the first piston portion is at least twice the diameter of the second piston portion, although any other first to second piston portion ratio can be selected depending upon the pressure increase or spring force constant desired. However, to maintain a constant spring force, the volume of the gas spring chamber should be sufficiently larger than the volume occupied by the piston at its full compression, preferably to about 4:1 ratio and greater.

A portion of the second piston extends past the gas spring chamber, with its free end coupled to or formed with a gas spring coupling mechanism. The energy mechanism further includes a trigger mechanism that operatively engages and disengages the coupling mechanism to hold the gas spring in its compressed condition and to release the gas spring from the compressed condition.

In one embodiment, the nozzle assembly and the gas spring are attached to a main housing which can be formed of any durable material capable of withstanding stress and strain subjected to, preferably a liquid crystal polymer. The energy mechanism further includes an actuating mechanism connected to the housing. The actuating mechanism holds the trigger mechanism and is movable relative to the housing. By engaging the coupling mechanism and moving the actuating mechanism away from the sleeve, the second piston portion is pulled out of the gas spring chamber while forcing the first piston portion into the gas spring chamber, further compressing the gas spring chamber.

In another embodiment, the gas spring and the trigger mechanism are contained in the housing while the actuating mechanism is movably connected to the housing.

The nozzle assembly is connected to the actuating mechanism so as to be movable along with the actuating mechanism. The actuating mechanism compresses the gas spring by pushing the first piston portion into the gas spring chamber. This moves the gas spring coupling mechanism into the trigger mechanism by which the gas spring is held in the further compressed condition.

The free end of the first piston portion is operatively connected to the plunger. Preferably, a lost motion connection mechanism is connected between the plunger and the first piston portion to provide a predetermined free play between the plunger and the piston. The lost motion connection mechanism thus enables the piston to move a predetermined distance before the piston pushes the plunger into the ampule chamber. For instance, the lost motion connection mechanism can comprise a tubular ram having a longitudinal slot occupied by a connector shaft of the plunger, allowing the shaft to slide relative thereto. The shaft can have a predetermined length to provide a predetermined gap between an end of the plunger and the end of the ram. The end of the ram can engage the plunger after the gap is first closed.

Alternatively, the lost motion connection mechanism can allow removable connection between the gas piston or the ram, if used, and the plunger, where one of the ends of the plunger and the first piston portion has a quick release resilient snap fitting connector and the other of the ends of the plunger and the first piston portion has a complementary engaging means such as an enlarged end or head portion or a channeled head having an enlarged head portion and an annual channel portion of a predetermined width. The lost motion connection mechanism according to the present may be made such that the force required to disconnect the plunger from the gas piston is substantially greater than the force required to move the pressure wall member away from said terminal wall during introduction of medication into said chamber.

Preferably, the lost motion connection mechanism is such that the plunger cannot be disconnected from the gas piston or the ram, if used, without first exposing the plunger, i.e., removing the nozzle assembly. In this regard, the connector has at least one snap fitting prong, four being preferable, each made of resilient material, which upon being attached to the enlarged head expands and returns to its original configuration once the end of the prong is connected to the enlarged head. Specifically, a tab extends from each prong which engages a shoulder portion of the enlarged head to maintain the engagement. The entire plunger, including the prongs, is confined within the ampule chamber. Although the prongs are dimensioned to slide inside the ampule chamber, the inner wall of the chamber confines the prongs from moving laterally outwardly to maintain the piston engaged to the plunger during use. The plunger is disconnected from the prongs by first unscrewing the nozzle assembly from the injector to expose the prongs. Since the prongs are no longer confined by the ampule chamber wall, the prongs can expand outwardly and release the enlarged head when it is pulled away therefrom.

Another aspect of the present invention includes a needleless injection device in which the housing can be formed in whole or in part of a durable plastic composition such as the aforementioned liquid crystal polymer, available under the trade name VECTRA®. Such composition allows for weight reduction and helps to eliminate lubrication that might otherwise be utilized in the assembly and operation of metallic housings.

Another aspect of the present invention includes a nozzle assembly that can be formed of a strong material capable of withstanding high pressure and stress such as gamma stabilized high impact polycarbonate, polypropylene and any derivatives thereof, or any medical grade material or composite capable of withstanding the pressure and stress subjected by the injector during use. The nozzle and the plunger can be made of the same material, including stainless steel. Specifically, the nozzle assembly comprises a main hollow cylindrical body terminating in a circular cone at one end and open at the opposite end, the inner wall of the body forming a cylindrical ampule chamber. The nozzle assembly includes external acme threading or any conventional fasteners to facilitate quick removal of or attachment to the injector. Grooves or any attachment means, such as cap mating surfaces for engaging the coupling device's quick release members described below can be formed around the outer side of the nozzle assembly to facilitate attachment of a medication filling device.

A plunger having a pressure wall contoured to the cone is positioned to slide within the ampule chamber. An end of the plunger opposite the pressure wall has a connector that can be removably engaged with an end of a piston or ram or the like as described above. A stop member can be provided at the end of the nozzle assembly if desired to retain the plunger therein during the disconnection of the nozzle assembly from the injector. Alternatively, the stop member can be omitted entirely if used with the quick release connector described above.

Another aspect of the present invention includes a coupling device for coupling a medication supply vial to a nozzle assembly of a needleless injection device or the like. The coupling device comprises a hollow main body having a first end and a second end opposite the first end. The main body is preferably cylindrical, but can be of any other configuration desired. A dividing wall having a first side and an opposite second side is positioned between the first and second ends. The first side is positioned closer to the first end than the second end, and the second side is positioned closer to the second end than the first end. The wall also has a throughhole. A hollow probe extends from the first side of the wall toward the first end, with its free end terminating within the main body such that it does not protrude beyond the first end. The probe is positioned to be in fluid communication through the throughhole.

A medication supply vial connector is formed on the first end for connecting to a medication supply vial, which permits insertion of said vial but prevents removal of said vial therefrom. A nozzle connector is formed on the second end, which has at least one quick release member that grabs a portion of the nozzle assembly, where the connection is made by pushing the connector toward the nozzle assembly and disconnecting made by a sufficient pulling and/or twisting force. The probe punctures through a vial seal upon connection of the vial to the nozzle connector and provides a fluid communication through the throughhole. The coupling device is coupled to a needleless injector simply by pushing it toward the nozzle assembly and is removed by simply pulling and/or twisting the same off the injector. When the vial is pushed towards the probe, the probe punctures through the seal and provides a fluid communication from the vial through the throughhole formed on the wall.

The coupling device further includes a stretchable diaphragm seal member positioned in abutting relationship with the second side of the dividing wall. The seal member can have a zero diameter opening generally in alignment with the throughhole, but preferably has an open aperture or hole. The zero diameter opening seals the throughhole until it is opened by stretching the seal member. The seal member abuts against the second side of the dividing wall to provide a liquid-tight seal between the nozzle assembly and the throughhole. A ring is preferably positioned in abutting relationship with the seal member. The configuration of the ring is complementary to the shape of the nozzle assembly to allow a precise alignment of the nozzle assembly to the coupling device. A protective cap is provided at the second end, which can be engaged with the ring and the quick release members to protect and close the second end. The cap has mating surfaces for engaging the quick release members.

The vial connector comprises at least one flexible tooth extending toward the wall, wherein an end of the tooth engages a portion of the supply vial. The supply vial has means cooperating with the tooth to prevent removal thereof from the coupling device. Preferably, the connector comprises a pair of flexible opposed teeth extending from the first end of the main body toward the first side of the dividing wall. The opposed teeth converge toward each other in the direction toward the dividing wall, where their free ends are configured to engage a portion of the supply vial to prevent the vial from being removed.

The nozzle connector preferably has a plurality of quick release members, each extending substantially parallel with the main body. The quick release members are resilient to expand radially away from each other during insertion of the nozzle assembly or the cap and to return substantially to its original relaxed condition when fully inserted. Each release member has a radially inwardly projecting portion that cooperates with the nozzle assembly for securement thereof.

Another aspect of the present includes a stepped gas spring described above which outputs a substantially constant force above, having a first piston portion extending axially outwardly at one end of the sleeve and the second portion extending axially outwardly at the other end of the sleeve in the opposite direction. One of the first and second piston portions includes a piston gripping means, preferably a circular groove or channel or the like formed around the one piston portion. The circular groove is preferably formed around near the free end of the second piston portion. The stepped gas spring further includes means for immobilizing the sleeve and for compressing the piston. The immobilizing and compressing means can be a needleless injector or a projectile launching device, which includes means for either pulling the second piston portion or pushing the first piston portion.

Another aspect of the present invention includes a projectile launching device for launching a projectile by a compressed air. The launching device comprises an outer hollow cylinder having a side wall and a closed end wall with an air discharging port. A barrel having a bore is connected to the cylinder, with the bore communicating with the port. A firing piston having a closed wall member is positioned within the hollow cylinder for movement therein. The closed end wall, the closed wall member and the side wall define a gas spring chamber. A stepped gas spring is connected to the firing piston for rapidly moving the firing piston toward the closed end wall to compress air within the firing chamber. The launching device includes a mechanism for forcing the firing piston away from the closed end wall and a trigger mechanism for maintaining the firing piston away from the closed end wall.

According to the present invention, the second piston portion is connected to the firing piston. The first piston portion extends axially outwardly at one end of the sleeve and the second piston portion extends axially outwardly at the other end of the sleeve in the opposite direction. A trigger engaging notch is formed on the second piston portion to engage the trigger mechanism and maintain the piston in an energized compressed state. An end of the first piston portion is connected to the firing piston.

BRIEF DESCRIPTION OF THE DRAWINGS

These and other features, aspects, and advantages of the present invention will become much more apparent from the following description, appended claims, and accompanying drawings in which:

FIG. 1 is a cross-sectional view of the needleless injector according to the present invention, with the actuating mechanism in the closed condition and the gas spring in its neutral condition.

FIG. 2 is a cross-sectional view of the needleless injector of FIG. 1, with the actuating mechanism in the extended condition and the gas spring in its energized condition.

FIG. 3 is a cross-sectional view of the needleless injector of FIG. 2, but with the gas spring in its neutral condition.

FIG. 4 is a cross-sectional view of another embodiment of a needleless injector according to the present invention, with the actuating mechanism in the extended condition and the gas spring in its neutral condition.

FIG. 5 is a cross-sectional view similar to FIG. 4, with the actuating mechanism in the closed condition and the gas spring in its energized condition.

FIG. 6 is a cross-sectional view similar to FIG. 5, but with the actuating mechanism in the open condition and the gas spring in its energized state, ready for firing.

FIG. 18 is a cross-sectional view of an air gun, with the firing mechanism in the armed and ready for firing condition.

FIG. 19 is a cross-sectional view similar to FIG. 18, with the firing mechanism in the unarmed, fired condition.

DESCRIPTION OF THE PREFERRED EMBODIMENTS

Figure 7:
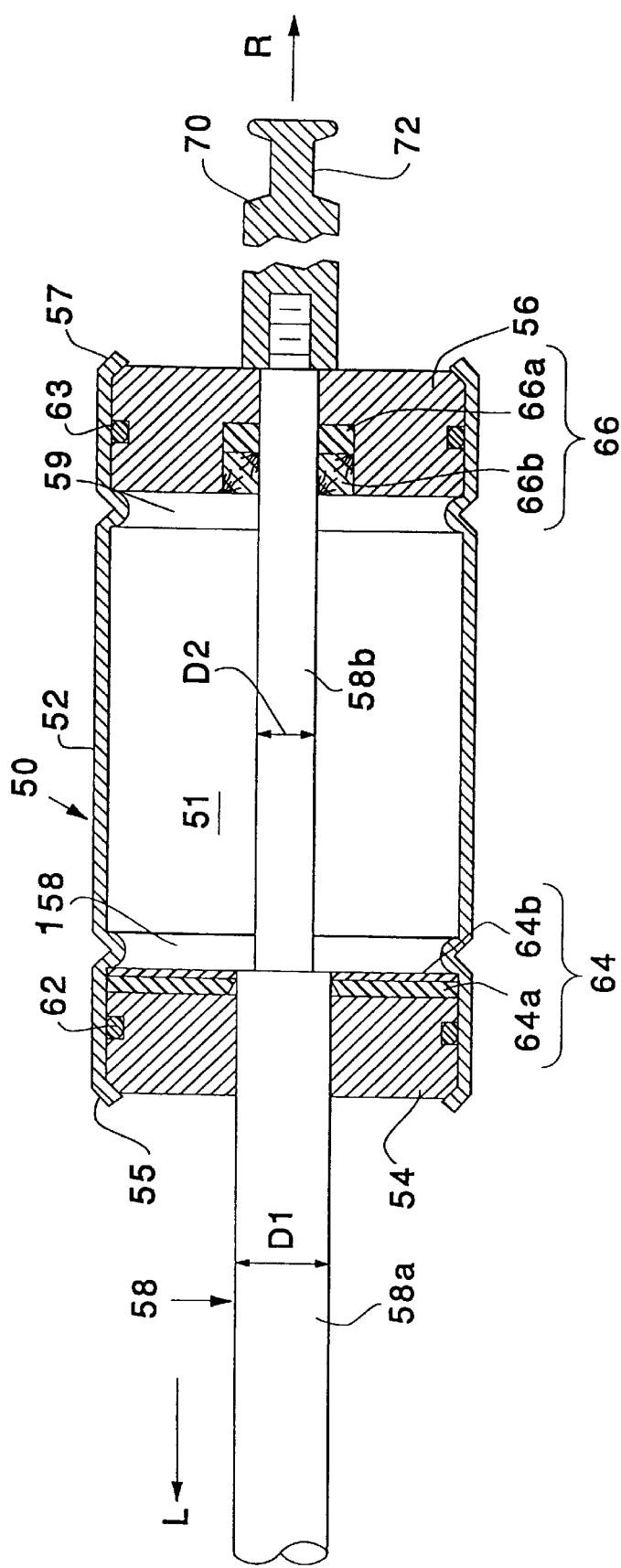
FIG. 7 is an enlarged cross-sectional view of the energy mechanism according to the present invention.

For convenience, the same or equivalent elements of the invention of embodiments illustrated in the drawings have been identified with the same reference numerals. Further, in the description that follows, any reference to either orientation or direction is intended primarily for the convenience of description and is not intended in any way to limit the scope of the present invention thereto. FIGS. 1–19 illustrate different embodiments of the present invention.

A needleless injection device 10 according to the present invention, referring to FIGS. 1–6, comprises a nozzle assembly 20, an energy source or mechanism 40 for forcing medication out of the nozzle assembly, and an actuating mechanism 90, 90A and a trigger assembly 100 for activating and triggering the energy mechanism 40. These components are operatively contained in a housing 200, 200A as shown.

The nozzle assembly 20 includes a nozzle member 22 having an orifice 24, preferably having a diameter about 0.07–0.4 mm, preferably of about 0.165 mm (0.0065 inches) or any other suitable diameter that would produce a uniform jet stream under a given desired pressure range and depth of injection. If a very uniform jet stream is desired, the orifice can be formed of a synthetic gem material, such as a synthetic ruby or sapphire, as disclosed in the '728 patent. It should be noted that the orifice means any type of opening, including a straight, convergent, divergent, convergent-divergent, etc. The nozzle assembly 20 can be threadably connected to the housing 200 or the actuating mechanism 90A such that it can be readily attached and detached, as better shown in FIGS. 10 and 11. Alternatively, other known structures for mounting or attaching two components can be utilized as well to detachably mate the nozzle assembly 20 to the housing 200. In this manner, the needleless injector 10 can be reused with various nozzle assemblies 20 that may contain different medications to allow for injection of various medications or medications of different doses either together or at different times. For instance, the nozzle assembly 20 can be prefilled with medication and disposed of after each use. Further, a medication filling device such as a coupling device 120 according to the present invention and the adapter described in the '113 patent, the disclosure of which is incorporated herein by reference, or any other coupling device can be used to fill the ampule chamber with medication.

The nozzle assembly 20, 20A shown in FIGS. 1–6 and FIG. 10 includes a cylindrical ampule chamber 26 terminating in a right circular cone 28. The nozzle assembly 20B shown in FIG. 11 also includes a cylindrical ampule chamber 26, but terminates in a convex cone 28' where the wall converges with a convex curvature. A plunger 30, 30A, 30B having a pressure wall contoured to the cone 28, 28' is positioned to slide within the ampule chamber 26. The plunger 30, 30A, 30B can include a sealing means such as an O-ring(s) or the like (not shown) formed around its outer periphery to provide a seal or the plunger itself can be a seal, as described, for instance in the '830 patent, the disclosure of which is incorporated herein by reference. The plunger can also include additional sealing means at spaced intervals to provide a better seal. In the embodiments shown, the plunger 30 is connected to a ram 32 which is connected to the energy mechanism 40. Alternatively, the ram 32 can be integrally formed with an energy mechanism if desired. In one embodiment, the plunger includes a connector shaft 31 having a ball end 31a. The ram 32 is connected to or integrally formed with an inertia mass 36 which in turn is connected to or integrally formed with the piston 58 of the gas spring 50. The inertia mass can be removably connected to the piston and the ram such that the mass can be adjusted to accommodate different types of injections, taking into consideration, for instance, the viscosity of the medication, the initial pressure build up desired, the strength of the gas spring 50 and the depth of injection penetration, etc. The piston 58 can also be directly connected with the plunger if desired.

If the nozzle assembly and the plunger are not disposable, they can be made of any durable inert material such as stainless steel. According to another aspect of the present invention, FIGS. 10 and 11 specifically illustrate different embodiments of disposable nozzle assembly 20A, 20B, including the plunger that can be made from a strong material capable of withstanding high pressure and stress such as gamma stabilized high impact polycarbonate, polypropylene and any derivatives thereof, or any medical grade material, including glass or composite thereof, compatible with the medication product and able to withstand the pressure and stress subjected by the injector. The nozzle assembly 20A, 20B preferably includes a conventional acme threading 25 to facilitate faster removal or attachment to the housing 220 or the actuating mechanism 90A. Grooves 27 or any attachment means can be formed around the outer side of the nozzle assembly 20A, 20B to facilitate the attachment of, for example, the present coupling device 120 or an adapter such as the one described in the '113 patent.

Figure 10:
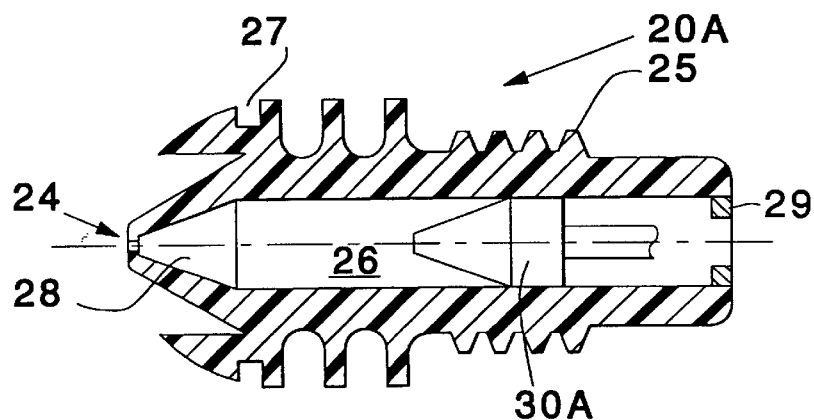
FIG. 10 is a cross-sectional view of another embodiment of a nozzle assembly according to the present invention.
Figure 11:
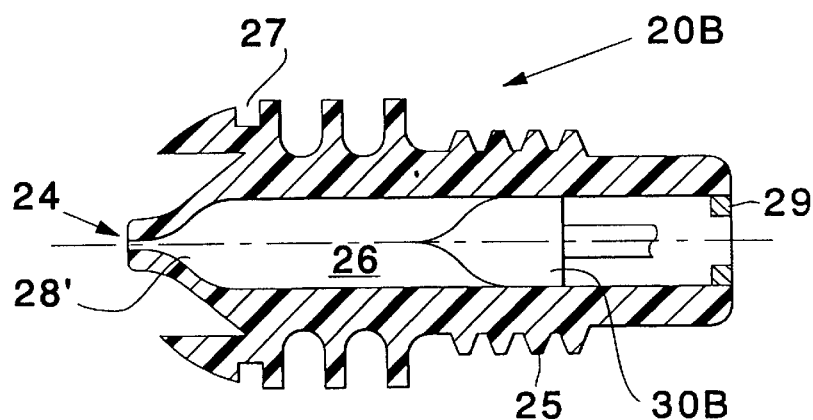
FIG. 11 is a cross-sectional view of yet another embodiment of a nozzle assembly according to the present invention.

It is desirable for the plunger 30A, 30B to be disposable with the disposable nozzle assembly 20A, 20B. In this regard, a stop member 29 can be provided within the end of the nozzle assembly 20A, 20B as shown in FIGS. 10 and 11 to retain the plunger therein when disconnecting the nozzle assembly from the housing 200, 200A or the actuation mechanism 90A. The stop member can engage the ends of the prongs 30a, for example. However, the stop member is dimensioned to enable the ram 32 or the first piston portion 58a to move into the ampule chamber 26. In this type of nozzle assembly, any conventional quick disconnecting means can be used which allows disconnection thereof by unscrewing the nozzle assembly from the injector and/or pulling the nozzle assembly with a force sufficiently greater than the force required to move the plunger during use so that the plunger can only be disconnected from the piston by a deliberate manual action.

Alternatively, the '830 patent describes such a disposable unit, the disclosure of which is incorporated herein by reference. Specifically, referring to FIGS. 12A–12C, the plunger 30C is substantially similar to the plunger 30, 30A and 30B, except that it has a resilient snap fitting connector 30a for removably connecting directly to the end of the first piston portion 58a. The connector 30a has at least one prong 30b, four being preferably and illustrated, each prong extending substantially parallel with the main body portion 30c. At the free end of each prong 30b, a lateral extension or tab 30d is formed, which extends radially inwardly toward the central axis thereof.

Figures 12A, 12D:
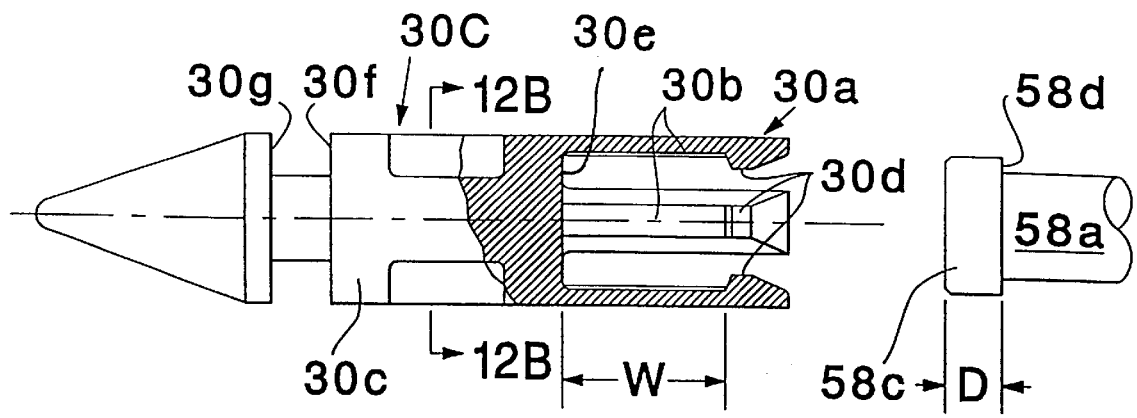
FIG. 12A illustrates a plunger having a quick connector for releasably mounting to the end of a piston in a gas spring according to the present invention, with a portion thereof illustrating a broken view taken along line 12A—12A of FIG. 12C.
FIG. 12D is a portion of a piston extending from the gas piston, with an enlarged end.
Figures 12B, 12C:
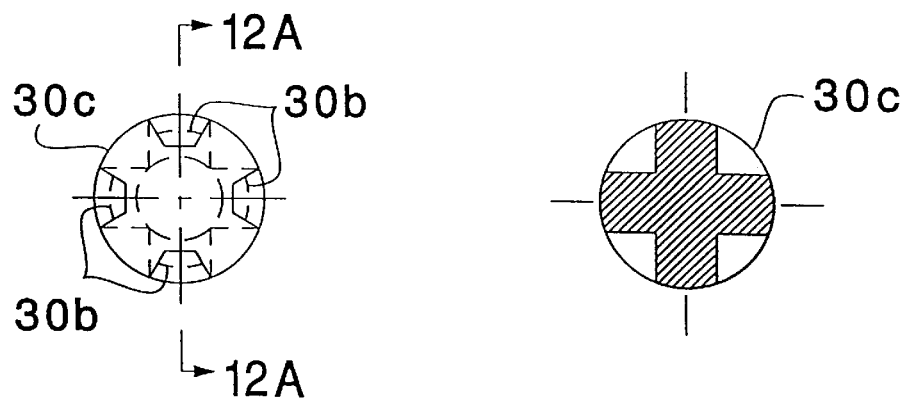
FIG. 12B is a cross-sectional view taken along line 12B—12B of FIG. 12A.
FIG. 12C is an end view of the plunger illustrated in FIG. 12A.

The first piston portion 58a illustrated in FIG. 12D has an enlarged free end 58c that engages with the prong to provide a desired length of free travel or lost motion. Alternatively, the first piston portion can also have an annular channel of a predetermined width adjacent an enlarged head, as disclosed in the '830 patent. The prongs 30b can be made of resilient material, which upon being first attached to the enlarged free end or head 58c, expand laterally outwardly to permit the free end to pass through the tabs 30d and return to its original configuration shown in FIG. 12A, once the enlarged end 58c passes the tabs. The thickness or depth D of the enlarged head is less than the width W provided between an end wall 30e and the tabs to allow free play or gap defined by W–D, a gap of at least about 3.5 mm being preferred. The enlarged end 58c is dimensioned to freely move relative to the plunger 30C within the gap, but prevented from being disengaged from the plunger during use. Specifically, the tabs 30d engage the shoulder portion 58d of the piston 58, and the entire plunger, including the prongs, is confined within the ampule chamber. Although the prongs are dimensioned to slide inside the ampule chamber the inner wall of the chamber confines the prongs from moving laterally outwardly, thus maintaining the piston engaged to the plunger during use. The plunger 30C is disconnected from the enlarged end 58c by first unscrewing the nozzle assembly from the injector to expose the prongs. Since the prongs are no longer confined by the ampule chamber wall, the prongs can expand laterally outwardly and release the enlarged end when it is pulled away therefrom. If the plunger 30C is used the nozzle assembly 20, 20A, no stop member 29 or the like should be provided in the ampule chamber 26 to allow insertion and removal of the plunger.

The spacing formed between the end wall 30f of the main body portion 30c and the end wall 30g of the pressure wall member can be provided to accommodate a sealing means such as an O-ring, as shown in the '830 patent.

The energy mechanism 40 includes a gas spring 50 for driving the plunger 30 so that the front wall thereof will force the medication out of the nozzle assembly ampule chamber 26. The gas spring 50 is positioned generally collinear with and spaced from the nozzle assembly 20. As more clearly shown in FIG. 7, the gas spring unit 50 includes a sleeve 52 with open ends, preferably cylindrically shaped or shape configured to the shape of the housing 200, 200A of the injector. The sleeve 52 is fixably or removably positioned within a cylindrical cavity 210 formed inside the housing. The open ends are closed using two end plugs 54 and 56, each having a central aperture in alignment with the longitudinal axis of the sleeve 52. The end plugs 54, 56 are fixedly disposed so that they do not move relative to the sleeve 52 through conventional retaining means. In the embodiment shown in the drawings, the end plugs are cylindrical, corresponding to the cylindrical inner periphery of the sleeve 52. The end plugs are positioned inside the sleeve 52 adjacent its open ends. Both of the open ends of the sleeve 52 are crimped, as shown in FIG. 7, toward the axis thereof to form circular stopping edges 55 and 57, respectively. These stopping edges prevent the end plugs from moving away from each other relative to the sleeve 52. In addition, abutment rolls 158 and 59 can be formed adjacent to the inner sides of the plugs, for instance by radially creasing the sleeve 52, to prevent the end plugs from moving toward each other. The stopping edges 55, 57 and the abutment rolls 158, 59 prevent the end plugs from moving in the axial direction relative to the sleeve 52. It is understood that other stopping or retaining means can also used to retain the end plugs 54 and 56 in position, such as screws, pins, adhesives, etc.

A stepped piston 58 is coaxially positioned relative to the sleeve and the end plugs such that the piston can slidingly move relative to the end plugs. The stepped piston 58 has a first portion 58a having a diameter D1 and a second portion 58b having a diameter D2, as shown in FIG. 7. In the preferred embodiment, the diameter D1 is at least twice the diameter D2. In this regard, the aperture formed in the end plug 54 needs to be larger to accommodate the first piston portion 58a.

The gas spring chamber 51, defined by the sleeve 52 and the end plugs 54, 56, is pressurized preferably using nitrogen or other inert gas having a relatively large molecule. Use of a gas with a relatively large molecule minimizes gas escape. This requires the end plugs to be sealed relative to the sleeve 52 and to the stepped piston 58. In this regard, to seal the end plugs 54, 56 against the sleeve 52, each of the end plugs is provided with a first seal, such as an O-ring 62, 63, positioned around a groove formed on the outer periphery of the end plug 54, 56. It is to be understood that the diameter of the O-ring is preferably slightly larger than the depth of each groove formed on the end plugs so that the O-ring is pressed tightly to sufficiently seal against the inner periphery of the sleeve 52. To seal the gas spring chamber 51 relative to the piston portion 58a, a second seal 64 comprising a disk 64a formed of a soft elastic material and a relatively rigid washer 64b is collinearly and contiguously positioned against the inner face of the end plug 54. The abutment roll 158 is positioned adjacent to the second seal to maintain the second seal in place. Similarly, a second seal 66 comprising a disk 66a formed of a soft elastic material and a relatively rigid retainer 66b can be collinearly and contiguously positioned within a cylindrical cavity formed within the end plug 56. The retainer 66b is positioned to immobilize the disk 66a. Instead of the retainer, a washer similar to the washer 64b can be used to immobilize the disk 66a. Alternatively, any conventional or known sealing mechanism can be used, which is well within the ambit of one skilled in the art.

A relatively highly pressurized gas spring requires seals to prevent gas from escaping through the piston 58. This may require a tight seal fitting which can create a mechanical friction, which in turn can slow the initial acceleration of the piston. Since the stepped piston 58 has to be capable of sliding relative to the second seals 64, 66, the seals should not be so tight as to prevent the piston 58 from moving. When compared to a coil spring, the gas spring has a slower initial acceleration due to this static friction. To compensate for this phenomenon, the present invention is provided with a lost motion connection mechanism between the ram 32 or the piston 58a and the plunger 30. As shown in FIGS. 2 and 6, a small gap 34 of preferably about at least 3.5 mm is provided between an end of the plunger 30 and an end of the ram 32 or the first piston portion 58a when the piston is pulled away from the sleeve 52 to the ready for firing configuration. This free play movement or the lost motion connection compensates for the initial slower reaction by delaying the engagement of the ram 32 or the first piston portion 58a to the plunger 30. The piston is not acted upon until the piston 58 has moved by the distance of the gap 34, at which point the ram 32 and/or the piston 58 have accelerated to its maximum or are approaching its maximum. Accordingly, when the ram engages the plunger, it has built up sufficient momentum to create the initial pressure necessary to pierce through the skin. According to the present invention, the gap 34 is adjustable as will be explained hereinbelow to vary the amount of the initial impact imparted on the plunger to generate desired peak pressure. The peak pressure can vary depending upon the viscosity of the medication, the injection penetration depth and other parameters which may affect the initial injection pressure output.

Figure 13:
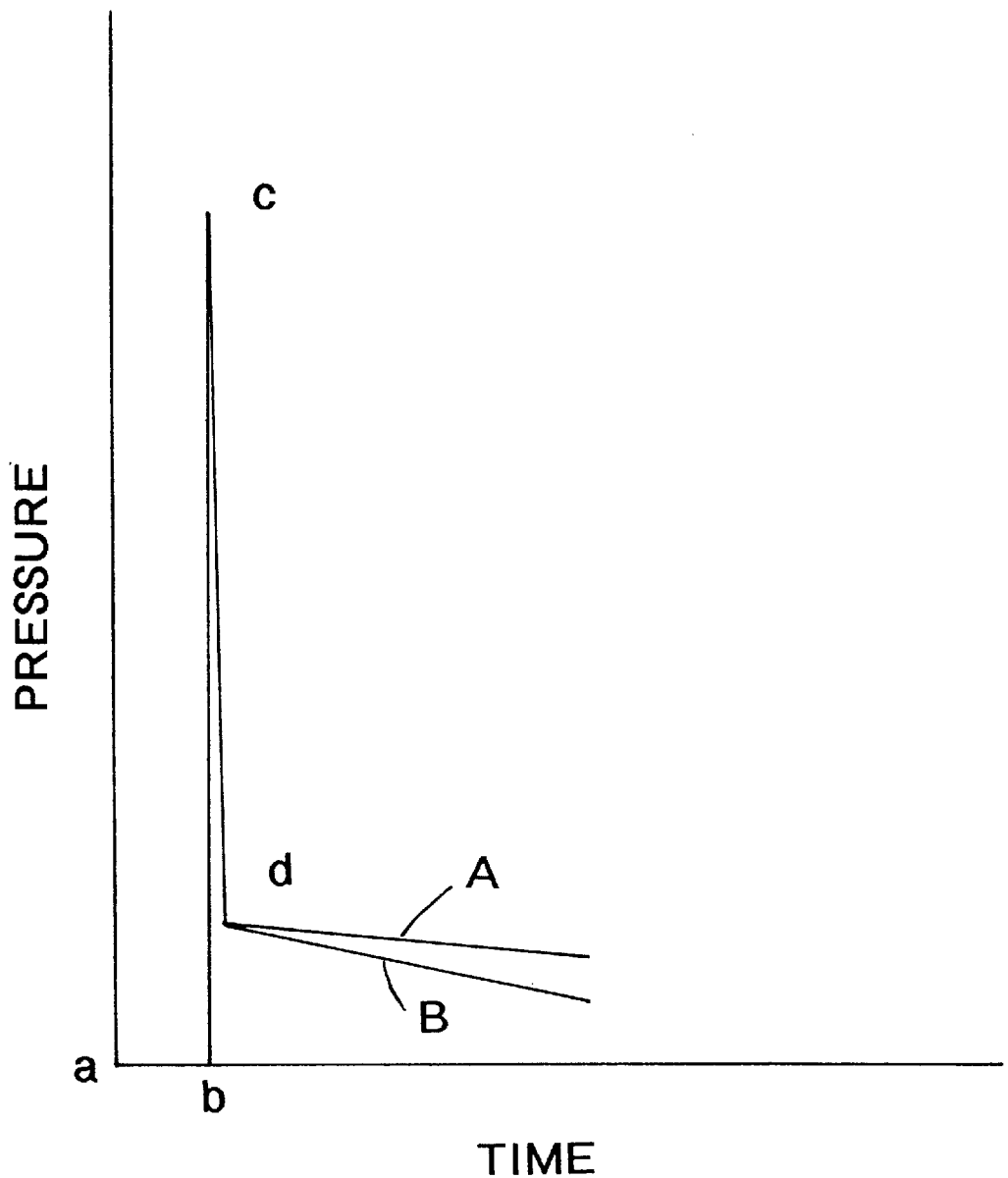
FIG. 13 is a schematic representative graph illustrating pressure-time curves for the gas spring injector relative to a coil spring injector.

A trigger extension or gas spring coupling mechanism 70 having a trigger engaging notch 72 is attached to the end of the second portion 58b, for example, by a threaded engagement. The end of the first piston portion 58a is connected to the inertia mass 36. However, the inertia mass can be omitted if the weight of the first piston portion is sufficient to generate desired initial momentum that would produce the level of the initial pressure build-up (at c as schematically shown in FIG. 13), required to penetrate the medication to the injection depth.

As previously discussed, the gas spring chamber 51 is relatively highly pressurized to a selective degree. The pressure in the gas spring chamber is inverse proportional to the volume. That is, if the volume of the gas spring chamber is decreased, then the pressure will proportionally increase by the reduction of the volume and vice-versa. Accordingly, when the piston 58 is either pulled or pushed in the direction of R relative to the sleeve 52, the piston portion 58a having a larger diameter than the piston portion 58b will occupy the space inside the gas spring chamber 51, consequently reducing the volume thereof. This causes the pressure in the gas spring chamber 51 to rise. If the piston is released, it will accelerate in the direction that will reduce the pressure in the gas spring chamber. Thus, the force exerted against the plunger 30 will be substantially equal to the force created by the increase of the pressure, minus the loss due to friction and heat.

Figure 9:
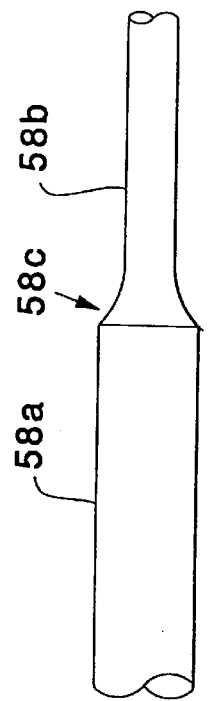
FIGS. 8 and 9 illustrate alternate embodiments of the piston for use in the needleless injector and the air gun according to the present invention.
Figure 8:
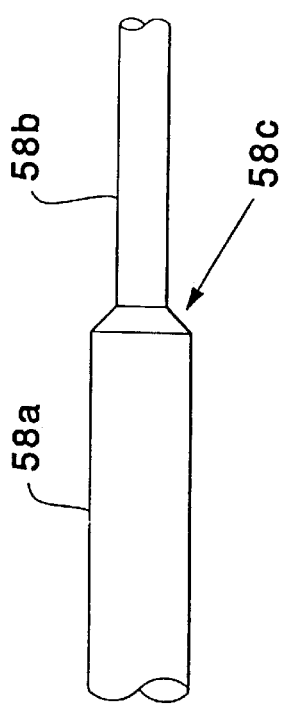

The junction 58c between the piston portions 58a and 58b can be stepped as shown in FIG. 7, or alternatively, it can be beveled as shown in FIG. 8, or curved as shown in FIG. 9. The differences among these configurations are negligible for the present purpose as the volume differences between these embodiments are relatively small.

In the embodiment of FIGS. 1–3, the energy device actuating mechanism 90 includes a trigger assembly 100 and actuating means for moving the trigger extension 70 along the directions L and R. This actuating mechanism 90 is tubular, with substantially cylindrical inner threading formed on the winding sleeve portion 92 thereof which threadably and coaxially engages with the counterpart outer threaded portion 220 formed on the housing 200. Specifically, the threaded portion 220 is formed at its outer periphery along the longitudinal length thereof. The winding sleeve portion 92 has cooperating threads 94 formed on the inner periphery along a portion of the longitudinal length thereof. By rotating the winding sleeve portion 92 in one direction relative to the housing, the distance between the trigger assembly and the sleeve 52 can be made larger and by rotating the same in the other direction, the distance can be made smaller.

As shown in FIGS. 1–3, the trigger assembly 100 comprises a latch housing sleeve 102 fixedly attached to the actuating mechanism 90. The latch housing sleeve 102 has a throughbore dimensioned to allow passage of the trigger extension 70. The sleeve 102 further has a plurality of sidewall openings 104 dimensioned to allow passage of balls or ball bearings 106. A tubular button 108 having one open end and a closed end is telescopingly positioned with the sleeve 102 as shown. The button 108 has a circumferential or annular groove 110 formed on the inner wall 109 thereof to allow portions of the balls 106 to engage the groove 110 when the trigger mechanism 100 is in the fired position as shown in FIG. 3 (not engaged with the trigger extension 70). The balls 106 are positioned so that it is substantially flush with the inner side wall surface 103 of the sleeve 102 as shown in FIG. 3 to allow the trigger extension 70 to pass through the sleeve 102. A latch ball retaining cup 112 is telescopingly positioned within the button 108 as shown in FIG. 3. A compression spring 114 is positioned between the cup 112 and the button 108 as shown in the FIGS. 1–3 to bias the button 108 and the cup 112 away from each other in the axial direction.

The housing 200, 200A and the actuating mechanism 90, 90A can be made of any durable material, including stainless steel, and plastics and any composite material, including plastic or composite material, with or without additives such as binders, fillers, fibers, carbon and the like, etc., well known to one of ordinary skill in the art. The weight of the injector can be reduced by using a lighter plastic material, rendering the device more user friendly since a lighter device can be more easily handled. The lighter weight will also allow persons to carry such injectors during daily travels and thereby allow for use wherever the person should need an injection. In one preferred embodiment, the plastic composition is a liquid crystal polymer available from Hoechst Celanese under the trade name VECTRA®, in particular VECTRA® A430 and A435. These compositions provide a high strength to weight ratio and offer the added advantage in that it can be processed relatively easily on both injection molding and extrusion equipment. In addition, these compositions include PTFE fluorocarbon or fluoropolymer for improved or enhanced lubricity to eliminate use of lubrication that would otherwise be used with metallic structures for assembly and/or operation.

In operation of the needleless injector of FIGS. 1–3, the sleeve portion 92 of the actuating mechanism 90 is rotated relative to the housing 200 from the condition shown in FIG. 3 to the closed condition shown in FIG. 1 to cause the trigger extension to engage the balls 106. Specifically, as the trigger mechanism moves toward the trigger extension 70, it first pushes the latch retaining cup 112 outwardly, causing the balls to engage the trigger engaging notch 72 formed on the trigger extension 70 as shown in FIGS. 1 and 2. Since the button is free to move outwardly, the spring 114 forces the button outwardly. The balls 106 are locked in the position between the notch 72 and the inner side wall 109 of the button as shown in FIGS. 1 and 2, locking the piston to the trigger. At this point, the trigger extension 70 is locked to the actuating mechanism such that rotation of the same to displace in the other direction (R) causes the piston 58 to move in the same direction R to further compress the gas spring chamber 51. As the piston is moved in the direction R, the plunger simultaneously draws medication (see below concerning the coupling device 120 for coupling a medication supply vial to a nozzle assembly of a needleless injector) into the ampule chamber 26. To purge any air that may be trapped in the ampule chamber, the injector is held upright and a small dose of the medication is first drawn into the chamber 26. Then, still maintaining the upright position, the medication is fully ejected out of the chamber 26 and into the vial or the connector can be disconnected to eject the same into a separate container for disposal, depending upon the application or any medication restriction. Any air contained in the chamber 26 is purged into the vial or the ambient. Then, the desired dosage of the medication is withdrawn into the chamber 26 without any air trapped in the chamber. The gap 34 can now be made narrower as desired without moving the plunger by rotating the sleeve portion 92 in the appropriate direction. It should be noted that the plunger cannot move until the gap is first closed or fully at its maximum. The injector is ready for firing. When the button 108 is pressed inwardly (toward the direction L), the groove 110 is positioned over the balls, releasing the trigger extension 72, causing the piston to accelerate in the direction that would purge the medication out of the ampule chamber 26. FIG. 3 shows the condition of the injector after it has been fired.

The embodiment shown in FIGS. 4–6 operates substantially similarly as described above with respect to FIGS. 1–3. However, whereas the piston 58 is pulled to energize the piston in the embodiment of FIGS. 1–3, the piston is pushed in the embodiment shown in FIGS. 4–6. Whereas the nozzle assembly 20 is connected to the housing 200 in the embodiment shown in FIGS. 1–3, the nozzle assembly 20 is connected to the actuating mechanism 90A in the embodiment shown in FIGS. 4–6.

Specifically, in the embodiment shown in FIGS. 4–6, the energy device actuating mechanism 90A is threadably connected to the housing 200A that holds the gas spring sleeve 52. The trigger assembly 100 is connected or contained in the housing 200A, but is not movable relative to the housing as in the embodiment shown in FIGS. 1–3. Again, the actuating mechanism 90A is tubular, with substantially cylindrical inner threading formed on the winding sleeve portion 92A thereof which threadably and coaxially engages the counterpart outer threaded portion 220A formed on the housing 200A. Specifically, the threaded portion 220A is formed at its outer periphery along the longitudinal length thereof. The winding sleeve portion 92A has cooperating threads 94A formed on the inner periphery along a portion of the longitudinal length thereof. By rotating the winding sleeve portion 92A in one direction relative to the housing 200A, the piston 58 can be pushed into the trigger assembly and by rotating the same in the other direction, the nozzle assembly is moved away from the piston.

In operation of the needleless injector shown in FIGS. 4–6, the sleeve portion 92A is first rotated relative to the housing 200A toward the trigger assembly 100 from the state shown in FIG. 4. This causes the plunger 30 to abut against the cone 28 of the nozzle assembly ampule chamber 26 and push the first piston portion 58a into the gas spring chamber 51, moving the second piston portion toward the trigger assembly until the notch 72 engages the balls 106, locking the gas spring in the fully energized state as shown in FIG. 5.

The sleeve portion 92A is now rotated in the other direction to draw the nozzle assembly away from the plunger and draw medication into the ampule chamber 26 into the state shown in FIG. 6. Again, to purge any air that may be trapped in the ampule chamber, the injector is held upright and a small dose of the medication is first drawn into the chamber 26 by rotating the sleeve portion in the direction that will move the plunger away from the orifice. This creates a vacuum in the ampule chamber, causing the medication to fill the ampule chamber. Then, still maintaining the upright position, the medication is fully ejected out of the chamber 26 and into the vial or the connector can be disconnected to eject the same into a separate container for disposal, depending upon the application or any medical restriction, by rotating the sleeve portion 92A in the direction that will move the plunger toward the orifice. Any air contained in the chamber 26 is purged into the vial or the ambient. Then, the desired dosage of the medication is withdrawn into the chamber 26 without any air trapped in the chamber. The gap 34 can now be made narrower as desired without moving the plunger by rotating the sleeve portion 92A in the appropriate direction. When the button 108 is pressed inwardly, the groove 110 is positioned over the balls, releasing the trigger extension 72, causing the piston to accelerate in the direction that would purge the medication out of the ampule chamber 26. FIG. 4 shows the condition after the piston has been released or fired.

According to the present invention, the injection pressure is maintained with a substantially less pressure drop than a corresponding coil spring injector to allow a faster injection time. Even though the stepped gas spring is not believed to be as efficient as a conventional gas spring which does not have a gas piston extending through both ends thereof, the stepped gas spring is superior to the coil spring as the injection pressure drop of the gas spring is less during the injection period than the coil spring. For example, a 75 lbs gas spring (approximate net output) can be formed with a gas spring chamber having a volume of 4698 $mm^3$, with an internal diameter of 13 mm and length of 35.4 mm is pressurized to 1,600 psi. A 3 mm diameter second portion 58b occupies the chamber for a length of 35.4 mm, occupying 250 $mm^3$ when it is in a fully extended state (neutral position). The approximate force constant can be calculated from the cross-sectional area working on the pressure. That is the cross-sectional area difference between the 7 mm portion and the 3 mm portion multiplied by the pressure ($(pi/4$ (49 $mm^2$–9 $mm^2$)$in^2$/645.2 $mm^2$)×1,600 $lbs/in^2$) to produce about 78 lbs, less some loss due to friction in the seals.

When the gas spring is fully compressed, a 7 mm diameter first portion 58a occupies the chamber for a stroke of 23 mm, occupying 885 $mm^3$, and the 3 mm diameter second portion 58b occupies the chamber for a length of 12.4 mm, occupying a volume of about 88 $mm^3$. Therefore, the volume of the chamber at full extension is about 4448 $mm^3$ and at full compression is about 3725 $mm^3$. In forming a substantially linear constant stepped gas spring, it is important to maintain the ratio between the volume of the gas spring chamber and the occupancy volume of the piston at full compression to about 4:1 and above. If the ratio falls below this level, then the gas spring can behave like a coil spring. Specifically, due to the volume of the chamber being too small relative to the occupancy volume of the first piston portion, the force required to compress the gas increases substantially as it is compressed further, similar to the compression force of the coil spring.

FIG. 13 illustrates schematic injection pressure-time curves comparing the present gas spring to a coil spring. $\underline{A}$ represents the gas spring curve and $\underline{B}$ represents the coil spring curve. When the injection device is fired, whether using a gas spring or coil spring, the pressure in the ampule chamber remains substantially the same as the atmospheric pressure from point $\underline{a}$ to point $\underline{b}$ as the piston starts to move until the piston or the ram closes any gap between the plunger and the piston or the ram. Then, the pressure builds up very rapidly from point $\underline{b}$ to point $\underline{c}$ for a very short duration. It reaches a peak at $\underline{c}$ just prior to the jet actually penetrates the epidermis. The injection pressure drops significantly from point $\underline{c}$ to $\underline{d}$ for both types of injectors, the injection actually occurring somewhere between points $\underline{c}$ and $\underline{d}$. What is significant in the present gas spring injection device is that the pressure at point $\underline{d}$ can be made about the same for both springs. However, the pressure at the end of the injection period for the gas spring is significantly higher than that of the coil spring. The gas spring can thus better sustain the initial pressure throughout its injection period, meaning less pressure loss.

Another advantage of the gas spring is that it can use a weaker gas spring, i.e., have a lower initial injection pressure (at $\underline{d}$). That is, with the coil spring, the initial pressure at $\underline{d}$ needs to be at a higher level to compensate for the faster decrease in the pressure throughout the injection period to avoid a wet injection.

A significant advantage of the gas spring injector is that it allows for a faster injection period for the same given dose as compared with the coil spring since there is a less loss of injection pressure for a given injection period.

Further, another advantage with the gas spring is that the pressure output does not significantly depend upon how much the piston 58 is pulled back with respect to the present injector shown in FIGS. 1–3. This means that the present invention can achieve a substantially uniform pressure throughout the injection period regardless of the dosage amount. With respect to the embodiment of FIGS. 1–3, even a small dosage injection, which only requires a small withdrawal of the plunger 30 from the ampule chamber 26 and thus the piston 58, can produce substantially the same constant pressure output as for a larger dosage injection that requires a larger withdrawal of the piston. This cannot be contemplated in a coil spring without moving to a significantly larger coil spring. That is, the coil spring operated injector requires a full compression of the coil regardless of the dosage level. Whereas the gas spring energization varies according to the dosage of the medication to be injected in the embodiment of FIGS. 1–3, the energization remains constant regardless of the dosage in the embodiment of FIGS. 4–6. The injector according to the present invention thus contemplates many different applications and uses.

Another advantage of the gas spring relative to the coil spring is that the winding energy remains relatively flat. That is, winding torque required to partially compress the gas spring is substantially the same as for fully compressing the spring. On the other hand, with the coil spring, the winding torque increases as the coil spring is compressed further and further, the output being inverse of the input effort.

Another advantage with the gas spring is that, starting from about point d, the gas spring does not produce significant initial pressure fluctuations, which are inherent in the coil spring. Such fluctuations are the result of the "slinky" or "ping-pong" effect, longitudinal oscillation produced in the coil spring.

Another advantage with the present gas spring is that the entire gas spring assembly can be readily replaced with another gas spring. In this regard, different strength gas springs can readily be replaced without altering the overall size of the injector. For example, a gas spring may have a force constant of 75 lbs can be replaced with a stronger or weaker force constant. The gas spring constant can be increased or decreased without altering the size of the gas spring. This can be accomplished by either changing the D1/D2 ratio or increasing or decreasing the pressure in the gas spring chamber, i.e., higher pressure results in a stronger gas spring and vice-versa. However, it should be noted that the ratio of the volume of the gas spring chamber and the volume of the piston occupied in the chamber when fully compressed be preferably about 4:1 and greater to maintain a minimum pressure drop. In this regard, the strength of the gas spring can be changed to accommodate different types of injections such as intradermal and intramuscular injections, as well as subcutaneous (fat tissue) and fascia (which overlies muscle) injections, or even through the muscle to the periosteum (bone surrounding tissue). The diameter of the orifice can accordingly be changed to accommodate different types of injections.

Another aspect of the present invention is a coupling device or adapter 120, as shown in FIGS. 14–17, for coupling a medication supply vial 122 to a nozzle assembly 20 of any needleless injector, including a coil spring operated injectors as shown for example in the '830, '543 and '818 patents, the disclosures of which are incorporated herein by reference, as well as the present gas spring injector and gas operated injectors described above. The medication supply vial 122 herein means any container for holding medication, regardless of the size, shape or form of the container. For example, the vial could be as shown herein, as shown in the '878, '483 and '113 patents, as well as an ampule, TUBEX® or any cylindrical container. The coupling device 120 comprises a generally elongated hollow cylindrical main body 124 having a first end 126 and a second end 128 opposite the first end 126. Although a cylindrical body is shown, any other body configuration can be used to accommodate various types of nozzle assembly and supply vial configurations. A dividing wall 130 having a first side 130A and an opposite second side 130B is positioned between the first end 126 and the second end 128. The first side 130A is positioned closer to the first end 126 than the second end 128, and the second side 130B is positioned closer to the second end 128 than the first end 126. A central hole 130C is formed through the dividing wall 130, which is generally collinearly aligned with a sharp-tipped hollow probe 132 extending therefrom between the first side 130A and the first end 126 to allow fluid from the vial to communicate through the wall 130. The probe 132 extends axially from the first side 130A toward the first end 126, but terminates within the main body such that it does not protrude beyond the first end 126 to prevent accidental sticking.

Figure 14:
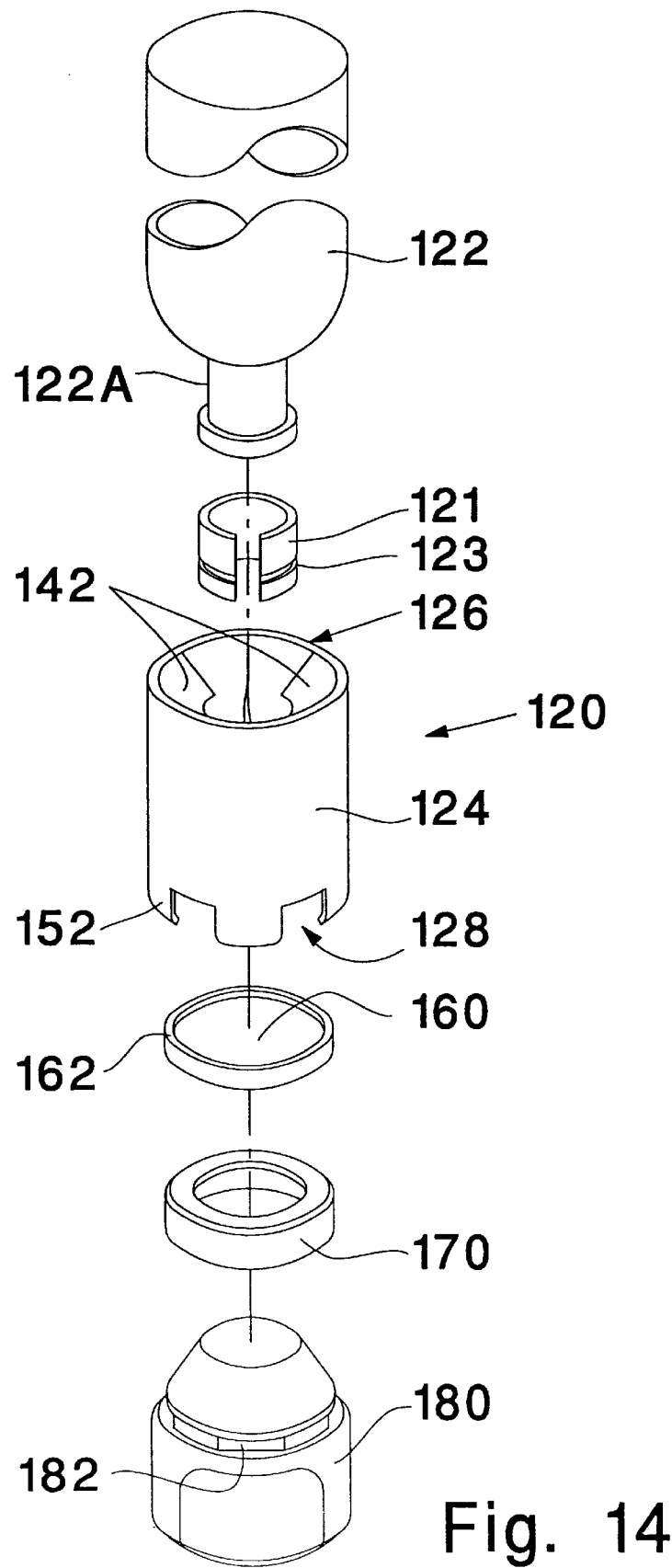
FIG. 14 is an exploded perspective view of the coupling device according to the present invention.
Figure 15:
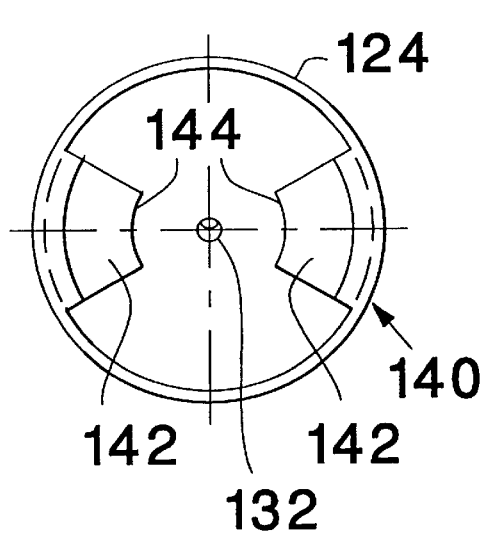
FIG. 15 is an end view of the coupling device of FIG. 14.

The first end 126 has a medication supply vial connector 140 to permit connection with the supply vial 122, but prevent removal thereof once connected. Specifically, the connector 140 comprises vial holders having a pair of flexible resilient teeth 142. Each tooth 142 is preferably tapered and defines a vial engaging free end 144. The teeth 142 are positioned diametrically opposite each other and extend inwardly and convergingly toward each other toward the wall 130. In the preferred embodiment, the ends 144 engage a neck portion 122A of the vial 122 which is preferably provided with means 121 cooperating with the teeth to prevent removal of thereof from the coupling device. For instance, the neck portion 122A could have a groove or a recess for engaging the ends 144 or could have a neck engaging sleeve 121 provided with an annular groove 123 as illustrated in FIG. 14. Alternatively, the vial could have an enlarged head followed by a narrower neck portion, as shown in the '878 patent. Any other alternate means that permits the vial to be inserted but make removal difficult can be used, i.e., one way connection.

When the vial 122 is inserted through the first end 126, the leading end (neck portion 122A) of the vial 122 forces the teeth 142 to spread apart. Once the neck portion or the head portion is inserted beyond or adjacent the free ends 144, the teeth 142 spring back to its original configuration, either engaging the recess 123 or the smaller neck portion 122A. The converging and biasing configuration of the teeth enables the recess 123 or the larger head to be abutted thereagainst to prevent the supply vial 122 from being removed in the opposite direction. Upon insertion of the leading end of the vial 122, the probe 132 punctures the seal thereof to provide a fluid communication through the passageway 132A formed therein.

Figure 16:
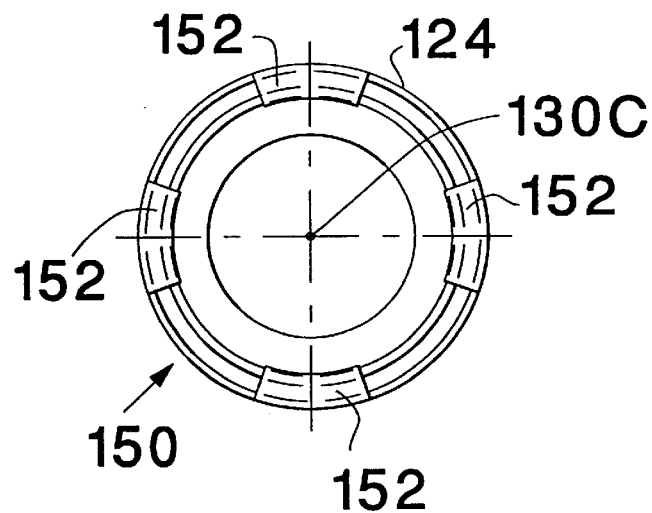
FIG. 16 is the other end view of the coupling device of FIG. 14.
Figure 17:
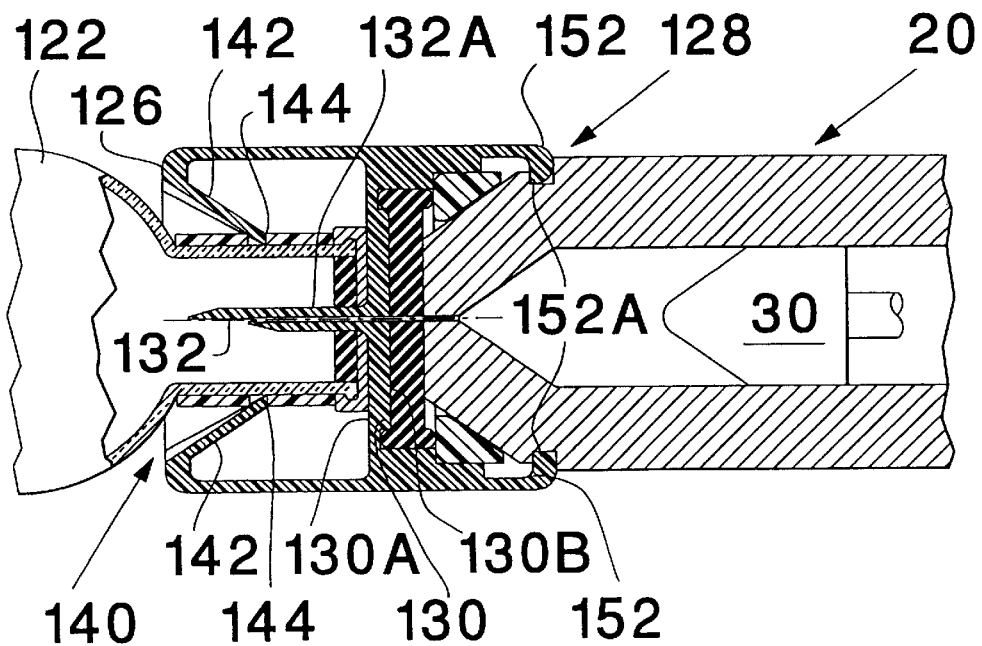
FIG. 17 is a cross sectional view of the coupling device of FIG. 14 coupled to a medical supply vial and a needleless injector.
Figure 16A:
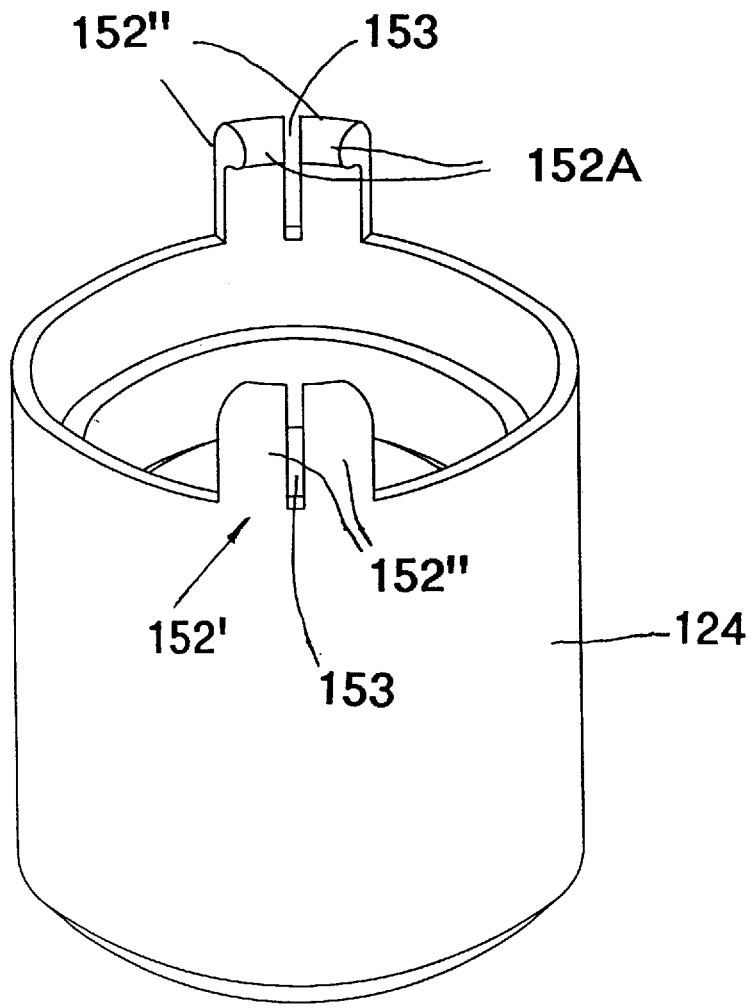
FIG. 16A is another embodiment of the coupling device illustrated in FIG. 14.

The second end 128 has a nozzle connector 150 having quick release members 152, 152' that automatically grab portions of the nozzle assembly 20 when the connector 150 is merely pushed into the nozzle assembly 20. Removal thereof is performed by pulling and/or twisting action. There can be four quick release members 152 evenly spaced (90° apart) around the periphery of the main body 124 as shown in FIGS. 14 and 16 or a pair of diametrically opposed members 152' as shown in FIG. 16A. In the embodiment of FIG. 16A, each member 152' is substantially similar to the member 152 shown in FIGS. 14 and 16, except that the member 152' is preferably slightly wider than the member 152 and has a slot 153 forming a pair of adjacent submembers 152", each of which can flex independently of the other. The release members 152, 152' extend substantially parallel with the longitudinal direction of main body as shown in FIGS. 14, 16A. The quick release members 152, 152' are resilient enable them to expand away from each other during insertion of the nozzle assembly and to return substantially to its original relaxed position when the same has been connected. However, it is preferable for the quick release members 152, 152' to be spread apart slightly when the nozzle assembly is connected to maintain a gripping force acting against the nozzle assembly, inwardly toward its neutral relaxed position. Each release member 152, 152' has a radially inwardly projecting portion or tab 152A that cooperates with the nozzle assembly 20 for securement thereof. The nozzle assembly can be formed with four complementary surfaces, recesses or notches, as shown for example by reference numeral 27 in FIGS. 12 and 13, which can be used with either two or four quick release members, to allow the projecting portion 152A to occupy the space therein and enable the coupling device to be securely attached to the nozzle assembly.

The coupling device further includes a stretchable diaphragm seal member 160 positioned in abutting relationship with the second side 130B of the dividing wall 130. The seal member 160 can have a zero diameter hole generally in alignment with the central opening. The zero diameter hole is formed by puncturing the seal member after it is first stretched, as described in the '113 patent, the disclosure of which is incorporated herein by reference. However, the seal member preferably has an open hole. To securely accommodate the seal member 160, the second side 130B of the dividing wall 130 is provided with a circumferential groove 130C. One side of the seal member 160 has a complementary circumferential ring portion 162 seated in the groove 130C.

A ring 170 is positioned in an abutting relationship with the seal member, with the ring frictionally engaged to the inner wall of the main body 124 to retain the seal member 160 in an abutting relationship to the wall 130. The configuration of the inner periphery 172 of the ring 170 is complementary to the outer contour of the nozzle assembly to allow a precise alignment of the nozzle assembly to the coupling device. When the nozzle assembly 20 is attached to the coupling device, it squeezes the seal member 160 against the dividing wall 130 to provide a liquid-tight seal between the nozzle assembly and the central opening.

A protective cap 180 is preferably connected to the coupling device, in engagement with the ring 170 and the seal member 160 to protect and close the second end 128. The cap 180 can have four complementary mating surfaces or recesses 182 which is substantially similar to the recesses 27 formed on the nozzle assembly to accommodate either the four or two quick release members. The recesses 182 receive the tabs 152 to securely hold the main body 124 to the cap 180.

The main body 124, including the medication supply vial connector 140 and the nozzle connector 150, and the ring 170 can be formed of a sterilized, non-toxic, any medical grade plastic composition such as polysulfone, polycarbonate resin, MOBAY MARKOLON 2658, GE LEXAN GR1310 or equivalents or any medical grade composition compatible with the medication. The seal member 160 is preferably formed of natural or synthetic rubber or the like.

The connecting member can be packaged with the cap 180 connected in place or separately provided. The cap 180 is first disconnected from the main body 124 if the cap came connected. A medication supply vial 122 is then connected to the other end of the main body 140. Once the vial is inserted, it cannot be removed without a substantial force. Alternatively, the vial can be first coupled to the main body, and then the main body with the vial can be coupled to the nozzle assembly after the cap is removed. When the nozzle assembly is connected to the coupling device, the hole in the seal member 160 is aligned with the orifice 24 formed in the nozzle assembly. In operation, the vial and the injection device is kept substantially at an upright stance to permit any air in the ampule chamber to escape through the orifice. As the plunger is drawn away from the nozzle assembly, a vacuum is created in the chamber 26, drawing the medication from the vial 122 through the hollow probe 132. When the desired amount of medication has been withdrawn, the coupling device is disconnected from the injector and the cap is attached to close the opening formed in the seal member 160. The connecting device, including the vial connected thereto can be saved for later use or discarded immediately if the medication instruction so indicates. In any event, the connecting device along with the vial is discarded as a unit when the vial becomes empty.

The coupling device according to the present invention provides a relatively low cost, disposable means of mating the medication supply vial to the injection orifice.

Another aspect of the present invention is an air gun or a device for launching a projectile by rapidly compressing air using the above described stepped gas spring. It is desirable to produce a uniform pressure at the compression chamber where the compressed gas propels the pellet through the barrel. As disclosed in the '517 patent, at high power levels, the flow of hot, compressed air produced by non-uniform acceleration appears to likely deform the pellet and thereby impair its accuracy. In addition, a problem known as "piston bounce," similar to the "slinky" effect described above, is common in air guns or spring operated guns. This problem is thought to have a detrimental effect on the accuracy. This bounce is caused by the air trapped between the piston crown and the front end wall of the outer cylinder at the end of the piston firing stroke.

These two common problems have been solved by the present invention. As previously described, the gas spring according to the present invention produces a substantially uniform output pressure, which in turn can uniformly apply compressive force to the firing chamber. In addition, as the energy stored in the gas spring is constant, unlike prior gas guns, the piston-bounce is eliminated since the trapped air in the firing chamber at that instance will unlikely be greater that the constant spring force of about 150 to 200 lbs. The greater details of an exemplary embodiment of an air gun incorporating the present gas spring is illustrated in FIGS. 18 and 19.

The illustrated air gun comprises a barrel 300 in front of a firing mechanism 310 mounted to a stock 303. The firing mechanism according to the present invention comprises an outer hollow cylinder 320, a hollow piston 330, and a gas spring 50'. The outer hollow cylinder 320 has a front end wall 322 with a discharge port 324 and a cylindrical side wall 326 fixedly attached to a receiver 329 or the like, within which the hollow piston 330 slides. The hollow piston 330 has a cylindrical piston wall 332 with a lug 334 extending from the outer side thereof as shown in FIGS. 18 and 19. The side wall 326 is provided with a longitudinal slot 328 through which the lug extends outwardly and moves in the longitudinal direction within the slot. One end of the side wall 332 has a closed end piston wall 336 while the opposite end is open. The outer side of the piston wall 332 has at least one O-ring seal 338 or the like. A firing chamber 340 is defined by the front end wall 322, the closed end wall 336 and the side wall 326, within which the air trapped therein is compressed when fired. Although not shown herein, the hollow piston can also have a soft lip ring seal as disclosed in the '686 patent.

The gas spring 50' is substantially similar to the one shown in FIG. 7. The hollow piston 330 is fixably connected to the free end of the larger piston portion 58a' such that the piston 58' moves in unison with the hollow piston 330. For purposes of using in an air. gun, the gas spring can be pressurized between 1500–2500 psi to produce about 150–200 lbs gas spring constant. Other pressures either greater or lower can be also used depending upon its application, i.e., propelling a projectile at a higher speed requires a greater pressure, and vice-versa.

The barrel 300 is pivotable about a pivot pin 302 or the like to enable opening of a barrel breach 304. The barrel is opened by pivoting the barrel 300 relative to the stock 301 in the direction shown by the arrow 308. This allows access to the breach for insertion of a projectile or pellet 306 and for cleaning the barrel. The breach has an O-ring seal 305 or the like to provide an air tight communication between the firing chamber 340 and the bore 301 of the barrel.

The barrel 300 is operatively linked to a cocking lever mechanism 310 such that when the breach is opened by pivoting the barrel in the direction shown by the arrow 308, the lever mechanism 310 moves in the direction shown by the arrow 314 to force the hollow piston 330 to the condition shown in FIG. 18. Specifically, an end 312 of the lever mechanism abuts against the lug 334 until a trigger mechanism 350 engages the notch 72' formed on an end of the smaller piston portion 58b'. A stop 360 is formed on or connected to the receiver 329 so that it is adjacent to and adjoining the lip 57' of the gas spring 50' to prevent the gas spring from moving rearward during the cocking step. The trigger mechanism 350 maintains the gas spring locked in the condition shown in FIG. 18 until fired.

While not specifically shown, the cocking mechanism for the present air gun can be a separate lever. Moreover, even a cocking mechanism similar to the actuating mechanism 90 shown in the present injector can be used to pull the hollow piston 330 rearwardly away from the front end wall 322. This enables adjustable power settings.

By moving the hollow piston 330 to the condition shown in FIG. 18, the larger piston portion 58a' is forced into the gas spring chamber 51'. Again, since the volume of the larger piston portion 58a' is greater than at its neutral extended condition shown in FIG. 19 where the smaller piston portion 58b' occupies therein, the gas spring chamber 51' is further pressurized. When the gun is fired, i.e., releasing the piston 58, the piston 58 and the hollow piston 330 rapidly accelerate toward the front end wall 322 under the force of the gas spring. Air in the firing chamber 340 is increasingly compressed until it exceeds a threshold at which the pellet is propelled out of the breach and through the barrel.

Moreover, although the present injector and the air gun have been exemplified using a stepped gas spring where the gas spring piston 58, 58' is movably positioned and the sleeve 52, 52' fixably held, the present invention can also be contemplated with the stepped gas spring piston 58, 58' fixedly positioned and the sleeve 52, 52' movably positioned. In this instance, the plunger 30 of the injector can be operatively propelled by the sleeve, at the end where the smaller piston portion 58b extends through the sleeve 52. To accommodate the piston, a cylindrical driving sleeve (not shown) can be coaxially positioned with the piston so that the driving sleeve propels the plunger 30. Similarly, the gas spring 50' can be reversely positioned such that the hollow piston 330 is driven by the sleeve 52' at the end where the smaller piston portion 58b' extends through the sleeve. This can be accomplished, for instance, by connecting the open end portion of the hollow piston 330 to the end of the sleeve where the smaller piston portion 58b' extends through.

Although the present invention has been described with respect to the stepped gas spring, the preferred embodiment thereof, any non-stepped gas spring can be used with the present needleless injector and the air gun. Gas springs similar to the ones taught by the Taylor et al. patents can be incorporated in the present injector, as well as any other conventional gas springs (non-stepped which does not have a piston extending through both ends) such as the ones produced by INDUSTRIAL GAS SPRINGS LTD., who also manufactures a stepped gas spring. For instance, the injector can utilize a gas spring having only the first piston portion 58a, with the other end completely sealed. The sleeve 52 can be stationarily held, with the first piston end connected to the plunger. The actuating mechanism can be connected as shown in FIGS. 4–6 to push the piston into the gas piston chamber. The trigger mechanism can be situated to engage the first piston portion between the sleeve and the end of the piston.

It should be understood that variations and modifications within the spirit and scope of the invention may occur to those skilled in the art to which the invention pertains. For instance, the injector can be modified to inject a solid medication through the skin or even to launch a projectile. Accordingly, all expedient modifications readily attainable by one versed in the art from the disclosure set forth herein that are within the scope and spirit of the present invention are to be included as further embodiments of the present invention. The scope of the present invention accordingly is to be defined as set forth in the appended claims.

What is claimed is:

1. A nozzle assembly for a needleless injection device having an energy source for propelling medication through said nozzle assembly comprising:

a generally hollow body defining a chamber having an end terminal wall with an orifice for passage of medication therethrough and an open end opposite said terminal wall, said body having means for removably connecting to an injection device;

a pressure wall member movably positioned within said chamber, said pressure wall member having means for sealing said chamber from said open end, wherein said pressure wall member is movable toward and away from said terminal wall to introduce and expel medication into and out of said chamber through said orifice; and a lost motion connecting mechanism for removably connecting said pressure wall member to an energy source and for providing a predetermined free travel distance between the pressure wall member and an energy source, said lost motion connecting mechanism including a resilient snap fit member which extends from said pressure wall member in a direction opposite said terminal wall, said snap fit member including a plurality of prongs, each prong extending from the pressure wall member and having a tab extending radially inwardly, said prongs forming a connection between said pressure wall member and an energy source, wherein said prongs are confined within said chamber and are dimensioned to slide inside said chamber with an inner wall of said chamber confining said prongs from moving laterally outwardly to maintain locking engagement between said pressure wall member and an energy source during use.

2. The nozzle assembly of claim 1, wherein said snap fit member defines a gap between the tabs of each prong and the pressure wall member so that when an energy source is associated with the prongs, the energy source is capable of traveling through the predetermined free travel distance across the gap to meet the pressure wall member.

3. The nozzle assembly of claim 2, wherein the gap is at least about 3.5 mm.

4. The nozzle assembly of claim 1, wherein said nozzle assembly is composed of a medical grade material.

5. The nozzle assembly of claim 4, wherein said nozzle assembly is composed of a material selected from the group consisting of gamma stabilized high impact polycarbonate, polypropylene, glass, and glass composite.

6. Nozzle assembly for a needleless injection device having an energy source for propelling medication through said nozzle assembly comprising:

a generally hollow body defining a chamber having an end terminal wall with an orifice for passage of medication therethrough and an open end opposite said terminal wall, said body having means for removably connecting to an injection device;

a plunger movably positioned within said chamber, said plunger having means for sealing said chamber from said open end, wherein said plunger is movable toward and away from said terminal wall to introduce and expel medication into and out of said chamber through said orifice; and a lost motion connecting means for removably connecting said plunger to an energy source, wherein said plunger is connected to an energy source by pushing said plunger toward an energy source and disconnected by pulling said plunger away from an energy source, wherein the force required to disconnect said plunger from an energy source is substantially greater than the force required to move said plunger away from said terminal wall during introduction of medication into said chamber, wherein said lost motion connecting means comprises a resilient snap fit member for association with an enlarged head of an energy source, said resilient snap fit member extending from said plunger in the direction opposite said terminal wall, wherein said snap fit member includes a plurality of prongs made of resilient material, which upon being attached to an enlarged head expand and return to their original configuration once said enlarged end is fully connected, with each prong extending from said plunger and, each of said prongs having a tab extending radially inwardly and confining an enlarged end connected to said plunger, wherein said entire prongs are confined within said ampule chamber, said prongs being dimensioned to slide inside said ampule chamber and an inner wall of said ampule chamber confining said prongs from moving laterally outwardly to maintain an enlarged end locked to said plunger during use.

7. The nozzle assembly of claim 6, wherein said snap fit member defines a gap defined between the tabs of each prong and the plunger so that when an enlarged end is positioned between the prongs, the enlarged end is capable of traveling a predetermined distance across the gap to meet the plunger.

8. The nozzle assembly of claim 6, wherein said nozzle assembly is composed of a medical grade material.

9. The nozzle assembly of claim 8, wherein said nozzle assembly is composed of a material selected from the group consisting of gamma stabilized high impact polycarbonate, polypropylene, glass, and glass composite.

10. A nozzle assembly for a needleless injection device having an energy source for propelling medication through said nozzle assembly comprising:

a generally hollow body defining a chamber having an end terminal wall with an orifice for passage of medication therethrough and an open end opposite said terminal wall, said body having means for removably connecting to an injection device;

a plunger movably positioned within said chamber, said plunger having means for sealing said chamber from said open end, wherein said plunger is movable toward and away from said terminal wall to introduce and expel medication into and out of said chamber through said orifice; and a lost motion connecting mechanism for removably connecting said plunger to an energy source and for providing a predetermined free travel distance between the plunger and an energy source, said lost motion connecting mechanism including a resilient snap fit member which extends from said plunger in a direction opposite said terminal wall, said snap fit member including a plurality of prongs, each prong extending from the plunger and having a tab extending radially inwardly, said prongs forming a connection between said plunger and an energy source, wherein said prongs are confined within said chamber and are dimensioned to slide inside said chamber with an inner wall of said chamber confining said prongs from moving laterally outwardly to maintain locking engagement between said plunger and an energy source during use.

11. The nozzle assembly of claim 10, wherein said snap fit member defines a gap between the tabs of each prong and the plunger so that when an energy source is associated with the prongs, the energy source is capable of traveling through the predetermined free travel distance across the gap to meet the plunger.

12. The nozzle assembly of claim 11, wherein the gap is at least about 3.5 mm.

13. The nozzle assembly of claim 10, wherein said nozzle assembly is composed of a medical grade material.

14. The nozzle assembly of claim 13, wherein said nozzle assembly is composed of a material selected from the group consisting of gamma stabilized high impact polycarbonate, polypropylene, glass, and glass composite.

* * * * *